United States Patent
Mullen et al.

(10) Patent No.: US 8,074,877 B2
(45) Date of Patent: Dec. 13, 2011

(54) SYSTEMS AND METHODS FOR PROGRAMMABLE PAYMENT CARDS AND DEVICES WITH LOYALTY-BASED PAYMENT APPLICATIONS

(75) Inventors: Jeffrey David Mullen, Pittsburgh, PA (US); Philip Yen, Cupertino, CA (US)

(73) Assignee: Dynamics Inc., Pittsburgh, PA (US)

( * ) Notice: Subject to any disclaimer, the term of this patent is extended or adjusted under 35 U.S.C. 154(b) by 272 days.

(21) Appl. No.: 12/339,058

(22) Filed: Dec. 19, 2008

(65) Prior Publication Data

US 2009/0159700 A1 Jun. 25, 2009

Related U.S. Application Data

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
*G06K 5/00* (2006.01)

(52) U.S. Cl. .................. 235/380; 235/375; 235/379

(58) Field of Classification Search .................. 235/487, 235/380, 375, 379
See application file for complete search history.

(56) References Cited

U.S. PATENT DOCUMENTS

| | | |
|---|---|---|
| 4,353,064 A | 10/1982 | Stamm |
| 4,394,654 A | 7/1983 | Hofmann-Cerfontaine |
| 4,614,861 A | 9/1986 | Pavlov et al. |
| 4,667,087 A | 5/1987 | Quintana |
| 4,701,601 A | 10/1987 | Francini et al. |
| 4,720,860 A | 1/1988 | Weiss |
| 4,786,791 A | 11/1988 | Hodama |
| 4,791,283 A | 12/1988 | Burkhardt |
| 4,797,542 A | 1/1989 | Hara |
| 5,038,251 A | 8/1991 | Sugiyama et al. |
| 5,168,520 A | 12/1992 | Weiss |
| 5,237,614 A | 8/1993 | Weiss |
| 5,276,311 A | 1/1994 | Hennige |
| 5,347,580 A | 9/1994 | Molva et al. |

(Continued)

FOREIGN PATENT DOCUMENTS

JP 05210770 A 8/1993

(Continued)

OTHER PUBLICATIONS

The Bank Credit Card Business. Second Edition, American Bankers Association, Washington, D.C., 1996.

(Continued)

*Primary Examiner* — Karl D. Frech

(57) ABSTRACT

A payment card (e.g., credit and/or debit card) or other device (e.g., mobile telephone) is provided with a magnetic emulator operable to communicate data to a magnetic stripe read-head. Data may include the type of reward that a user would like to earn as a result of making a purchase or the type of reward that a user would like to utilize to at least partially pay for a purchase.

21 Claims, 22 Drawing Sheets

U.S. PATENT DOCUMENTS

| | | |
|---|---|---|
| 5,361,062 A | 11/1994 | Weiss et al. |
| 5,412,199 A | 5/1995 | Finkelstein et al. |
| 5,434,398 A | 7/1995 | Goldberg |
| 5,434,405 A | 7/1995 | Finkelstein et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,585,787 A | 12/1996 | Wallerstein |
| 5,591,949 A | 1/1997 | Bernstein |
| 5,608,203 A | 3/1997 | Finkelstein et al. |
| 5,623,552 A | 4/1997 | Lane |
| 5,657,388 A | 8/1997 | Weiss |
| 5,834,747 A | 11/1998 | Cooper |
| 5,834,756 A | 11/1998 | Gutman et al. |
| 5,856,661 A | 1/1999 | Finkelstein et al. |
| 5,864,623 A | 1/1999 | Messina et al. |
| 5,907,142 A | 5/1999 | Kelsey |
| 5,913,203 A | 6/1999 | Wong et al. |
| 5,937,394 A | 8/1999 | Wong et al. |
| 5,955,021 A | 9/1999 | Tiffany, III |
| 5,956,699 A | 9/1999 | Wong et al. |
| 6,025,054 A | 2/2000 | Tiffany, III |
| 6,045,043 A | 4/2000 | Bashan et al. |
| 6,076,163 A | 6/2000 | Hoffstein et al. |
| 6,085,320 A | 7/2000 | Kaliski |
| 6,095,416 A | 8/2000 | Grant et al. |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,308,890 B1 | 10/2001 | Cooper |
| 6,313,724 B1 | 11/2001 | Osterweil |
| 6,389,442 B1 | 5/2002 | Yin et al. |
| 6,393,447 B1 | 5/2002 | Jakobsson et al. |
| 6,411,715 B1 | 6/2002 | Liskov et al. |
| 6,446,052 B1 | 9/2002 | Juels |
| 6,460,141 B1 | 10/2002 | Olden |
| 6,592,044 B1 | 7/2003 | Wong et al. |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,752,321 B1 | 6/2004 | Leaming |
| 6,755,341 B1 | 6/2004 | Wong et al. |
| 6,764,005 B2 | 7/2004 | Cooper |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,223 B2 | 5/2006 | Wong |
| 7,044,394 B2 | 5/2006 | Brown |
| 7,051,929 B2 | 5/2006 | Li |
| 7,083,094 B2 | 8/2006 | Cooper |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparinl et al. |
| 7,356,696 B1 | 4/2008 | Jakobsson et al. |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,426 B2 | 9/2009 | Osterweil et al. |
| 7,591,427 B2 | 9/2009 | Osterweil |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,828,207 B2 | 11/2010 | Cooper |
| 2001/0034702 A1 | 10/2001 | Mockett et al. |
| 2001/0047335 A1 | 11/2001 | Arndt et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0120583 A1 | 8/2002 | Keresman, III et al. |
| 2003/0034388 A1 | 2/2003 | Routhenstein et al. |
| 2003/0052168 A1 | 3/2003 | Wong |
| 2003/0057278 A1 | 3/2003 | Wong |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0226899 A1 | 12/2003 | Finkelstein |
| 2004/0035942 A1 | 2/2004 | Silverman |
| 2004/0133787 A1 | 7/2004 | Doughty |
| 2004/0162732 A1 | 8/2004 | Rahim et al. |
| 2004/0172535 A1 | 9/2004 | Jakobsson |
| 2004/0177045 A1 | 9/2004 | Brown |
| 2005/0021400 A1 | 1/2005 | Postrel |
| 2005/0043997 A1 | 2/2005 | Sahota et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0116026 A1 | 6/2005 | Burger et al. |
| 2005/0119940 A1 | 6/2005 | Concilio et al. |

| | | |
|---|---|---|
| 2005/0154643 A1 | 7/2005 | Doan et al. |
| 2005/0228959 A1 | 10/2005 | D'Albore et al. |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner |
| 2006/0131396 A1 | 6/2006 | Blossom |
| 2006/0161435 A1 | 7/2006 | Atef et al. |
| 2006/0163353 A1 | 7/2006 | Moulette et al. |
| 2006/0174104 A1 | 8/2006 | Crichton et al. |
| 2006/0176410 A1 | 8/2006 | Nose et al. |
| 2006/0196931 A1 | 9/2006 | Holtmanns et al. |
| 2006/0256961 A1 | 11/2006 | Brainard et al. |
| 2007/0034700 A1 | 2/2007 | Poidomani et al. |
| 2007/0063025 A1 | 3/2007 | Blossom |
| 2007/0114274 A1 | 5/2007 | Gibbs et al. |
| 2007/0124321 A1 | 5/2007 | Szydlo |
| 2007/0152070 A1 | 7/2007 | D'Albore |
| 2007/0152072 A1 | 7/2007 | Frallicciardi et al. |
| 2007/0153487 A1 | 7/2007 | Frallicciardi et al. |
| 2007/0174614 A1 | 7/2007 | Duane et al. |
| 2007/0192249 A1 | 8/2007 | Biffle et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0267504 A1 | 11/2007 | Beeson |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0096326 A1 | 4/2008 | Reed |
| 2008/0126398 A1 | 5/2008 | Cimino |
| 2008/0128515 A1 | 6/2008 | Di Iorio |
| 2008/0148394 A1 | 6/2008 | Poidomani et al. |
| 2008/0201264 A1 | 8/2008 | Brown et al. |
| 2008/0209550 A1 | 8/2008 | Di Iorio |
| 2008/0288699 A1 | 11/2008 | Chichierchia |
| 2008/0294930 A1 | 11/2008 | Varone et al. |
| 2008/0302877 A1 | 12/2008 | Musella et al. |
| 2009/0013122 A1 | 1/2009 | Sepe et al. |
| 2009/0036147 A1 | 2/2009 | Romano |
| 2009/0037275 A1 * | 2/2009 | Pollio ............................ 705/14 |
| 2009/0046522 A1 | 2/2009 | Sepe et al. |
| 2009/0078777 A1 | 3/2009 | Granucci et al. |
| 2009/0108064 A1 | 4/2009 | Fernandes et al. |
| 2009/0150295 A1 | 6/2009 | Hatch et al. |
| 2009/0152365 A1 | 6/2009 | Li et al. |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0290704 A1 | 11/2009 | Cimino |
| 2009/0303885 A1 | 12/2009 | Longo |
| 2011/0028184 A1 | 2/2011 | Cooper |

FOREIGN PATENT DOCUMENTS

| | | |
|---|---|---|
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2008064403 | 6/2008 |

OTHER PUBLICATIONS

A Day in the Life of a Flux Reversal. http://www.phrack.org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, Apr. 28, 2009.
U.S. Appl. No. 60/594,300, Poidomani et al.
U.S. Appl. No. 60/675,388, Poidomani et al.
English translation of JP 05210770 A.

* cited by examiner

1600 http://www.bank.com

Welcome Jeff,
Below is the what your new configuration of your Loyalty Selection card will look like when code is entered

3  LED
1  0  2
   4

A  Hilton
B  $-Back
C  Charity 1
D  Charity 2

1234 – 5678 – 9012 – 3456
HOLO
LOGO

Jeffrey Mullen
Issued: 1/08, Expires: 1/12

1610

Enter code 15343342 or hold card up to the following flashing triangle
1630
1620

FIG. 16

SYSTEMS AND METHODS FOR PROGRAMMABLE PAYMENT CARDS AND DEVICES WITH LOYALTY-BASED PAYMENT APPLICATIONS

CROSS-REFERENCE TO RELATED APPLICATIONS

This application claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

A material may be sandwiched between the two layers to assist in reducing the effect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card. Accordingly, a coil may be fabricated so that the coil wraps around an interior material.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, alloys). A material, for example, may have a permeability multiple times greater than the permeability of a vacuum. A material, for example, may have a relative permeability of 2 to 25,000. A material may include, for example, a permalloy, iron, steel, ferrite, nickel or any other material. A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB layer or other layer). A similar and/or different material may be placed either above and/or below a portion, or the entire, set of paths on a layer for a coil. Accordingly, a material may be placed in the interior of a coil as well as along a side of the coil.

Displays may be provided near user interfaces or other structures. For example, a display may be provided next to an LED. Cards may be programmed during manufacturing so that these displays may display particular information. Accordingly, for example, the same card architecture may be utilized to provide a number of different types of cards. A user may utilize user interfaces (e.g., mechanical or capacitive interfaces) to change the function of the display. For example, codes may be entered to reconfigure the displays. Alternatively, for example, a user may utilize buttons to select information to be displayed on displays associated with user interfaces. A code may associate a name of a store with a button and/or a dollar amount. For example, a display may be configured to read "Target $50." Information may be entered manually, but also may be received by a card. For example, a user may swipe a card a second time through a magnetic stripe reader and receive information via a magnetic emulator. This received information may be utilized to update information on the card (e.g., the balance of a gift card, credit account, and/or debit account). Information may also be received by an RFID antenna and/or IC chip located on a card and in communication with a central processor (or distributed processors). For example, transaction information (e.g., list of past transactions, stores where transactions occurred, amounts of transactions) and account information (e.g., balance information, bill information, amount due information) may be communicated to the card and displayed on one or more displays.

A dynamic card may be manufactured in a variety of ways. For example, a dynamic card may be printed onto a flexible material (e.g., a flexible polymer). Multiple layers of this material may be bonded together to form a multiple layer flexible structure. This multiple layer structure may be laminated (e.g., via hot, warm and/or cold lamination) to form a card. The card may be programmed before or after lamination. A card may be programmed via a direct connection between a programmer and one or more contacts on a card. A card may be programmed via a capacitive, optical, or inductive communication via a communications link between a programmer and one or more components (e.g., a contact) on a card. Accordingly, for example, a card may be laminated and capacitively programmed. After programming, a processor on the card may be signaled to burn-out its programming communication channel(s) such that no further programming may occur. A portion of the card may not be laminated. Accordingly, a programmer may connect to this non-laminated portion of the card. The non-laminated portion of the card may be laminated after programming. Alternatively, for example, the non-laminated portion of the card may be cut after programming (e.g., and after the processor burns-out its programming ports so the processor cannot be further programmed).

Additional external communication devices may be provided on a card. For example, a USB port or Wi-Fi antenna may be provided on a card. Such additional external communication devices may, for example, allow a user to communicate with stationary computer, laptop, or other device. Such communication devices may, for example, be utilized to load gift cards, or other information (e.g., transactional or account information) from a laptop to a card or other device. A card is provided that includes a light sensor such that information can be communicated to a card via light (e.g., via a light transmitted from a TV or website).

A loyalty-based payment application may be provided on a card. For example, a user may earn reward points when that user purchases an item using the payment card. In this manner, a user may earn reward points based on the type of item, the dollar amount of the item, and/or the time during which the item was purchased. A remote server may receive information indicative of reward points that a particular user has earned. This remote server may also transmit information back to a card (e.g., via a payment card reader). Such information may include the total amount of reward points that have been earned by a particular reader. The total amount of reward points may be stored on a payment card and displayed to a user via a display located on the card automatically after each transaction and/or as a result of manual input.

A user may provide manual input to a card in order to instruct the card to pay for a purchase using reward points. A purchase may be subsequently authorized in a variety of ways. For example, a flag may be placed in payment information that is communicated through a payment card reader that is indicative of a user's desire to utilize reward points for payment. Such a flag may take the form of a particular character or set of characters in a particular location of payment information. A remote server may then, for example, look for a particular character, or set of characters, in received payment information to determine whether payment is desired to be made by reward points. Alternatively, for example, a different payment account number may be communicated when reward points are desired and a remote server may utilize this different payment account number to authorize a payment transaction. Payment information that is communicated may be encrypted in a variety of ways. For example, all or part of the payment information may be encrypted for each transaction, which may be determined via manual input or read-head detectors, or based on time.

Multiple different types of rewards may be earned on a card. For example, a user may be provided with the option of earning reward points, airline miles, receive cash-back, or donating a purchase-based value to charity. In this manner, a card may be provided with a set of buttons where each button corresponds to a different type of reward. Additional buttons may be provided for additional functionalities (e.g., the entry of a user's Personal Identification Number). Before a purchase, a user may select the type of rewards that the user would like to earn for the purchase. Data corresponding to the selection may be provided in payment information communicated to a payment card reader. Such rewards information may take many forms. For example, data indicative of the selection may be provided as discretionary data. Alternatively, for example, a different account number may be communicated for each type of reward.

Payment information may be communicated in a variety of ways. For example, information indicative of the type of reward that is desired or the form of payment may be communicated via an IC chip, RFID antenna, and magnetic emulator or encoder. Payment information may be structured differently for each type of communication and, similarly, may include overlapping as well as different data. For example, data indicative of the type of reward desired may be provided as discretionary data in both track 1 and track 2 of a magnetic emulator. However, for example, data indicative of the type of reward desired may be provided as a different account number for a transaction based off an RFID signal from an RFID antenna. Data may be stored on a memory and constructed by a processor such that the payment information may delivered via a reader communication device.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 15 is an illustration of a webpage constructed in accordance with the principles of the present invention;

FIG. 16 is an illustration of a webpage constructed in accordance with the principles of the present invention;

DETAILED DESCRIPTION OF THE INVENTION

Figure 1:
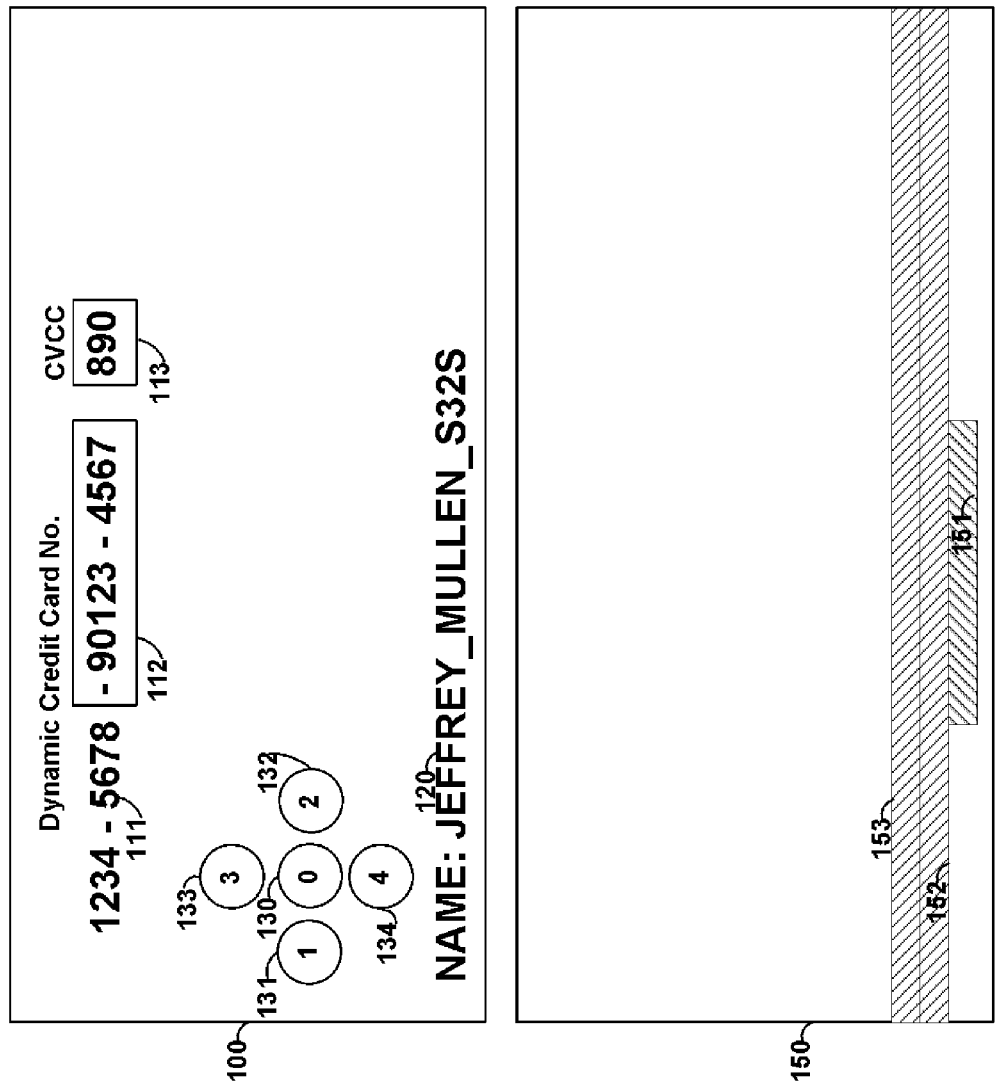
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card. Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 kHz.

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
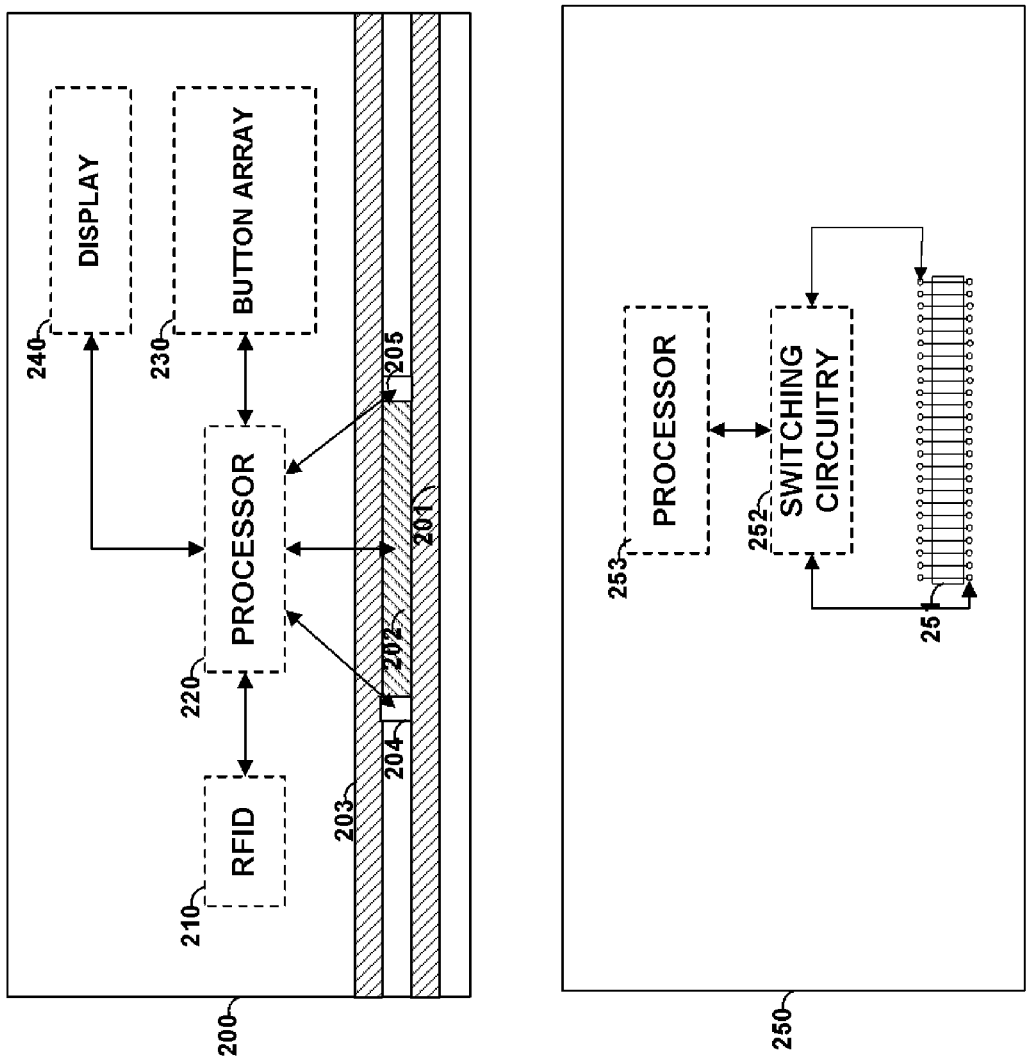
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-to-zone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil. Switching circuitry 252 may include, for example, one or more transistors that may be utilized to control the direction of current via emulator 251 (e.g., the polarity of voltage(s) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

Figure 3:
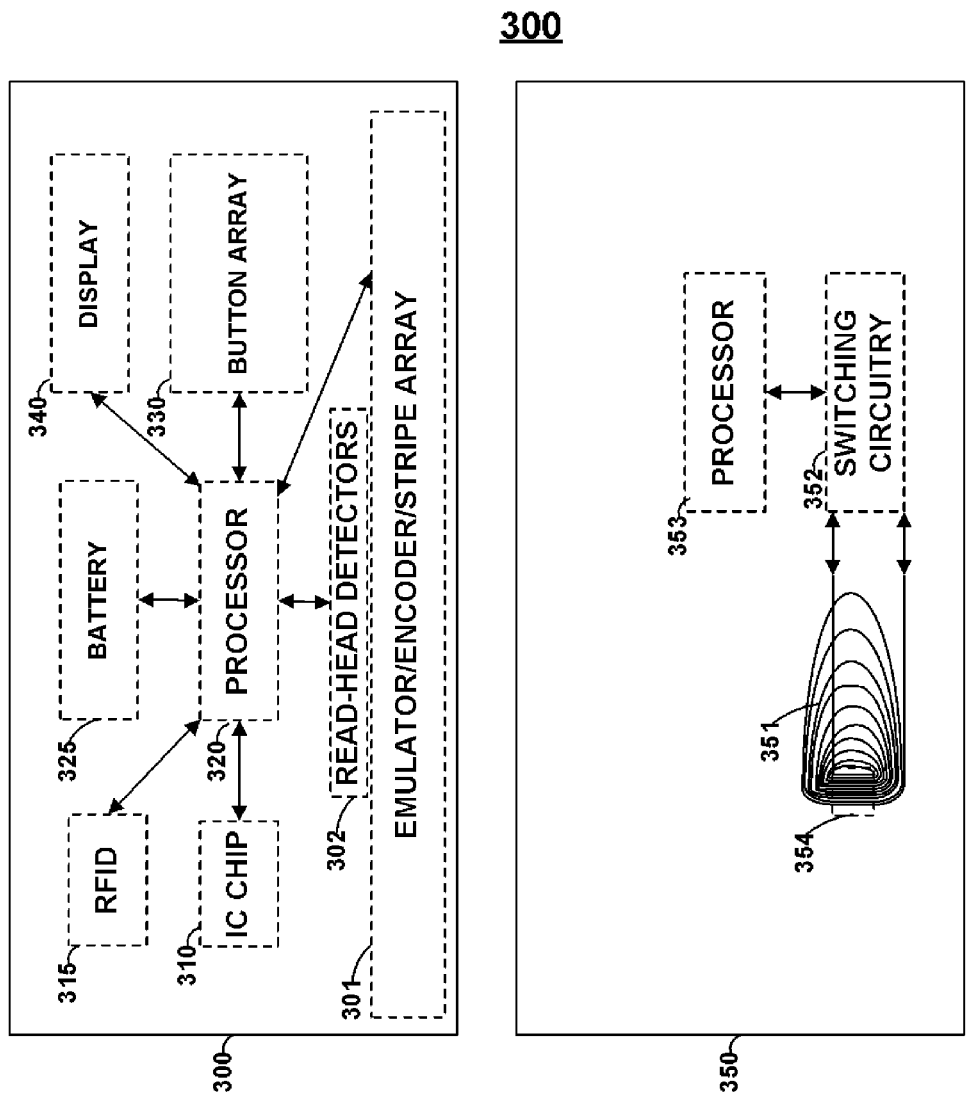
FIG. 3 is an illustration of cards constructed in accordance with the principles of the present invention.

FIG. 3 shows card 300 that may include a number of components. Card 300 may include one or more processors 320. A processor may include, for example, cache memory, RAM, and/or ROM. Additional memory may be provided on card 300. For example, additional non-volatile, volatile, cache memory, RAM, and/or ROM may be provided on card 300. Battery 325 may be provided on card 300. Battery 325 may be, for example, a lithium polymer battery and may have a thickness less than a millimeter (e.g., approximately 0.5 mm). RFID antenna 315 may be provided on card 300 and may communicate data to an RFID reader. Persons skilled in the art will appreciate that an RFID may be included that is a passive or active RFID. IC chip 310 may be included on card 300 and may communicate data to an IC chip reader. Device 301 may be included to communication information to a magnetic stripe reader. Device 301 may include any number of magnetic emulators, magnetic encoders that encode magnetic stripes, and/or magnetic stripes. For example, device 301 may include a magnetic emulator for one track of magnetic data and a magnetic stripe for a second track of data. Alternatively, for example, device 301 may include two emulators for separate tracks of data. An emulator may, for example, communicate information to a read-head of a magnetic stripe reader serially. One or more read-head detectors 302 may be provided to detect a read-head (or other attribute) of a magnetic stripe reader. Additional detectors may be included to detect, for example, when a card is provided into an IC chip reader and/or an electromagnetic field from an RFID reader. Button array 330 may be provided, for example, to receive input from a user. Button array 330 may include any number of buttons (e.g., 4, 5, 10, or more than 10). Button array 330 may include, for example, mechanical buttons, capacitive buttons, or any type of user interface. One or more displays 340 may also be included. A display may be, for example, an electronic ink display (e.g., electrochromic display), LCD display, or any other type of display. Display 340 may be flexible.

Display 340 may be printed onto a layer during a printed fabrication process (e.g., PCB). Additionally, for example, battery 325 may be printed onto a layer during a printed fabrication process (e.g., PCB). Similarly, a magnetic emulator may be printed onto a layer during a printed fabrication process (e.g., PCB). Other components may be printed onto a layer during a printed fabrication process (e.g., PCB) such as capacitive read-head detectors, and capacitive touch sensors. Accordingly, a display, battery, read-head detector, and button array may be printed on one or more layers that are bonded together and laminated.

FIG. 3 shows card 350 that may include, for example, processor 353, switching circuitry 352, and emulator 351 having active region 354. Switching circuitry 352 may, for example, control the direction of current through emulator 351 in order to change the direction of electromagnetic fields generated by emulator 351 such that data may be communicated serially to a magnetic stripe read-head. Persons skilled in the art will appreciate that emulator 351 may be fabricated on a single layer and that region 354 may include coil segments dense enough to generate an electromagnetic field that can be recognized by a read-head of a magnetic stripe reader.

Figure 4:
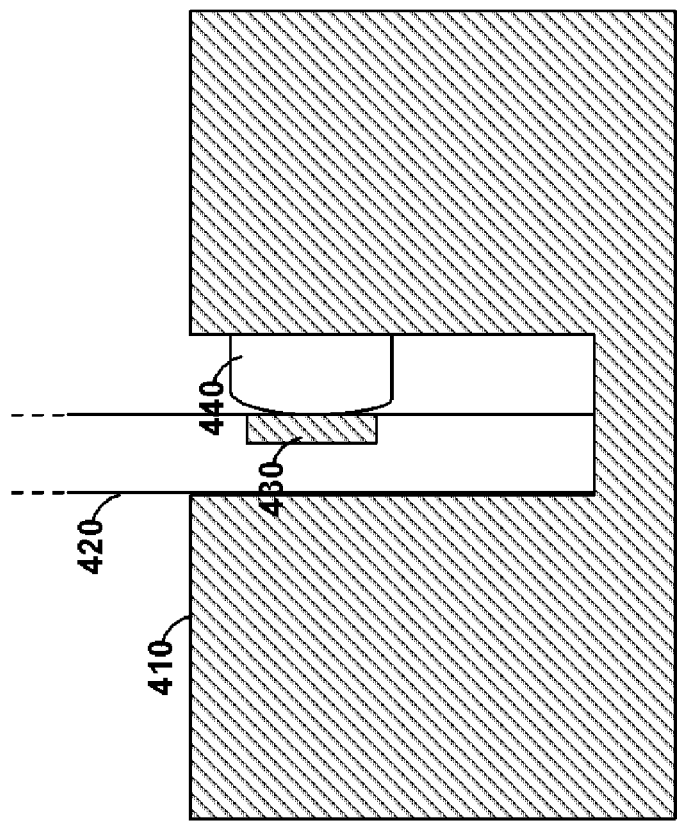
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
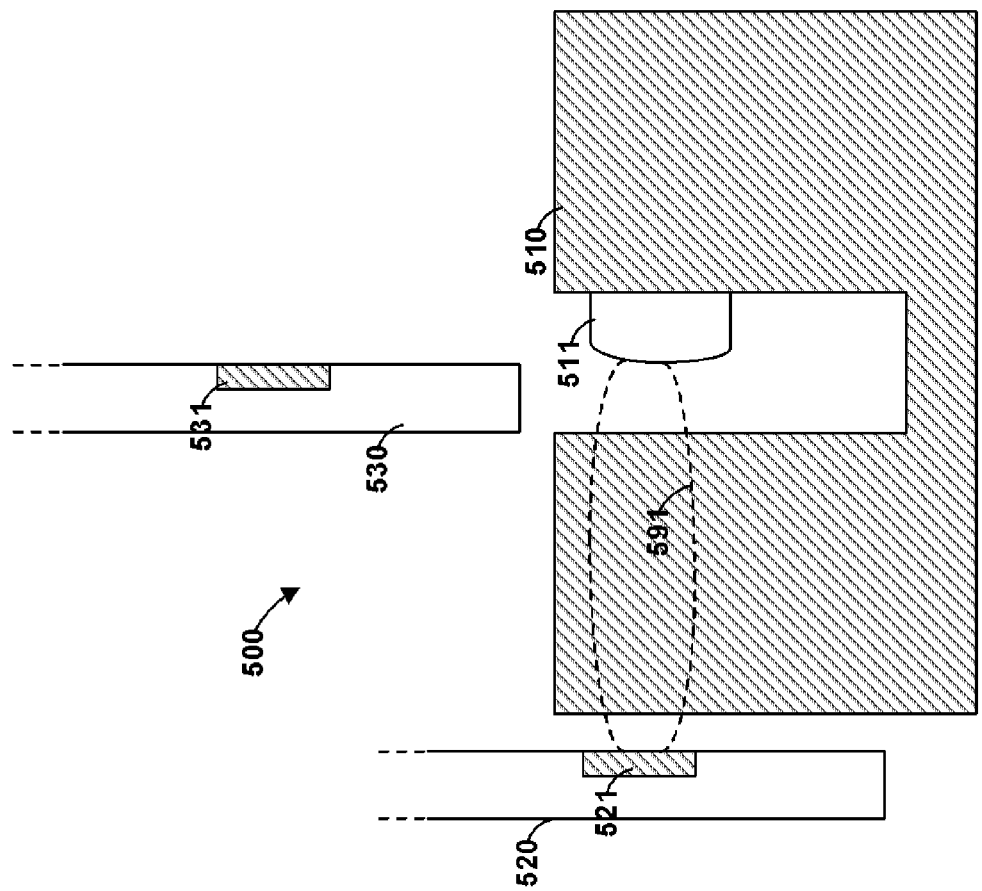
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0").

Figure 6:
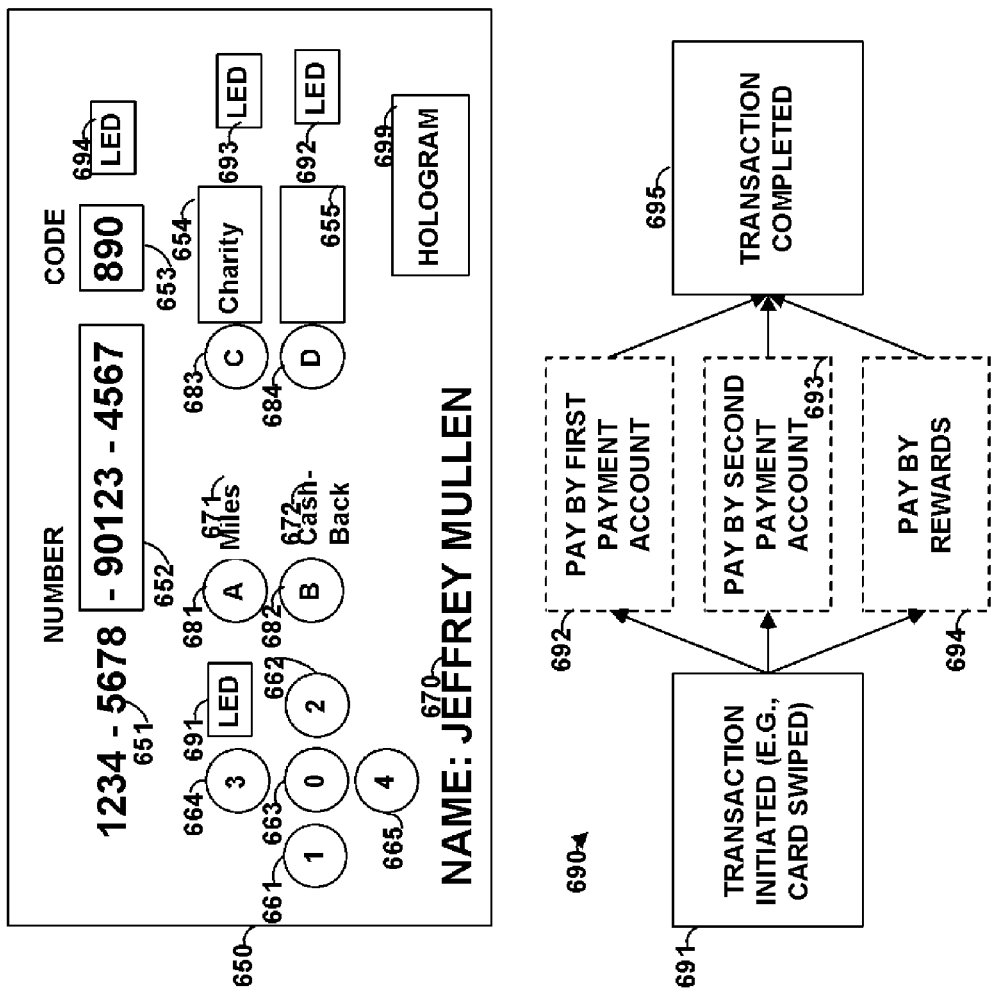
FIG. 6 is an illustrations of a card and a payment process constructed in accordance with the principles of the present invention.

FIG. 6 shows card 650 that includes buttons 651-664, light sources 691-694, displays 852-853, permanent information 651 and 670, buttons 681-684, and hologram 699. A user may be provided with a payment number. Such a payment number may be comprised of permanent data, dynamic data, or a combination of permanent and dynamic data. Dynamic data may be provided, for example, on display 652. Display 653 may be utilized to provide a code, which may be dynamic. Such a code may be utilized in authorize a transaction. Persons skilled in the art will appreciate that displays may display a code, payment number, or any type of data that changes based on time or based on use (e.g., utilizes one-time use data). Similarly, data may be static and may not change. Accordingly, for example, a display may be utilized to display the same data when desired such that the data may be hidden when the data is not desired to be displayed. Buttons 651-664, 681-682, and/or 683-684 may be utilized to signal a processor to display information on display 652, display 643, or display 652 and display 653.

A Personal Identification Code (PAC) may be entered to utilize to display data, as well as instruct a processor to provide particular data. For example, a particular PAC may provide one payment number (e.g., a credit card number) while a different PAC may provide a different payment number (e.g., a debit card number). A PAC may include a sequence of button presses (e.g., 5 particular button presses). Furthermore, a PAC may be utilized to unlock a card so that the card may be utilized. For example, buttons 681, 682, 683, and 684 may not be utilized by a user until an appropriate PAC has been entered via buttons 651-665. A number may be changed based on time (e.g., via display 652, display 653, or display 652 and display 653). Accordingly, a PAC may be entered such that the particular number associated with a particular button (e.g., a number associated with button 651) for a particular time period (e.g., a particular day) may be displayed. One PAC may activate display 652 while another PAC may activate display 653.

Light source 691 may be an LED or other source of light. Light source 691 may display light each time a button associated to light source 691 is pressed (e.g., buttons 661-662). Similarly, light source 692 may display light each time a button associated with light source 692 is pressed (e.g., button 681 or 682). Light source 693 may display light each time a button associated with light source 693 is pressed (e.g., light source 683 or 684). Light source 694 may be associated to a component and may display light each time that component is activated (e.g., display 653 or 652 is activated). Light sources may emit light having different colors. For example, a processor may determine that a PAC provided to the processor via buttons 661-665 matches a valid PAC for performing an operation. Each button press may cause light source 691 to emit light of a first color (e.g., YELLOW). The last button press to complete the PAC, however, may cause light source 691 to emit a different color if the PAC is VALID (e.g., emit GREEN) yet emit another color if the PAC is INVALID (e.g., emit RED). Particular areas of a laminated card may be transparent such that light from a light-source illuminates the transparent area.

Buttons may be provided on a card that each may, for example, be associated with a card of a particular country. Persons skilled in the art will appreciate that a card may be provided with a default number. Such a default number may include, for example, permanent data 651 and data displayed on display 652. Accordingly, a particular PAC may display the default data on display 652.

Persons skilled in the art will appreciate that other default data may be provided to other components of a card upon entry of a PAC. For example, particular default data (e.g., payment card number and discretionary data) may be communicated to a magnetic emulator (or magnetic encoder) such that the information may be communicated to a magnetic stripe read-head. Similarly, default data (e.g., payment card number and discretionary data) may be communicated to an RFID antenna, an IC chip, or an RFID antenna and an IC chip. Such default data may be different for each component (e.g., magnetic encoder/emulator, RFID antenna, IC Chip) and may be in different formats (e.g., one track of payment data for one magnetic emulator and another track of payment data for another magnetic emulator).

Button 681 may cause, for example, display 652, display 653, or display 652 and 653 to display data associated to button 681. Similarly, data associated to button 681 for other components of card 650 (e.g., a magnetic emulator, magnetic encoder, RFID antenna, and IC chip) may be communicated through those components. Button 681 may be associated with, for example a particular territory (e.g., America). Accordingly, for example, information communicated via card 650 may be associated with a default country upon entry of a particular PAC until, for example, a button is pressed associated with a different country. At this time, for example, the information communicated by card 650 may change to the information associated with the particular button pressed.

A button may be utilized to provide instructions to a processor that a gift card is desired to be utilized via card 650. A gift code may be entered (e.g., via buttons 661-665) after a particular button is pressed such that a user may, for example, associate a gift card to that particular button of card 650. Accordingly, card 650 may be utilized to make a gift purchase such that the original gift card may be thrown out (or left at home). The code entered into card 650 may be utilized, for example, to provide a processor with a number to transmit via the card (e.g., next time the particular is utilized). Such a number (as well as associated data such as associated discretionary data) may be communicated by card 650 via one or more displays, magnetic emulators, magnetic encoders, RFID antennas, and IC chips. A code may alternatively, for example, transmit a flag (e.g., discretionary data) that a gift card is being utilized (e.g., upon another use of the particular button) such that a server may look at a seller ID number and check if there are any gift cards associated to a particular payment card number for that seller ID number. Accordingly, for example, a user may obtain a gift card (e.g., Target gift card) and may link that gift card to his/her payment card account (e.g., credit card account) and may utilize a button to send a flag that a gift card is desired to be utilized. A code may be entered to provide a particular flag (e.g., a flag associated with a particular seller). Alternatively, no code may be entered and a particular may just be utilized to generate a generic flag (e.g., causing a server to check if there are any linked gift cards for the account associated with the seller associated with the utilized point-of-sale reader). A user may be provided with a particular code to be entered when utilize the gift card at an online store (e.g., Target's online store). The online store may, for example, allow a user to enter his/her payment information (e.g., credit card number, expiration date, name on card, zip code associated with card) and allow the user to select whether a gift card should be utilized associated with that card (e.g., via a radio button or other webpage input structure).

A button may be provided on card 650 and may be utilized, for example, to make an in-store purchase. The button may activate, for example, a particular display to display information for an in-store purchase (e.g., a portion of an account number). For online transactions, a different button may be pressed and a code may be displayed. In not showing an online code for an in-store purchase, for example, a user that is provided with a card during an in-store purchase may not gain access to the additional code information. Persons skilled in the art will appreciate, for example, that such a code (may be transmitted via a component (e.g., emulator) even though the information is not displayed. Moreover, for example, both the code and partial (or full) account number may be the same display only displayed when different buttons are pressed. A different code may be communicated through a communications component (e.g., magnetic emulator, magnetic encoder, RFID antenna, or IC chip) such that the code cannot be intercepted and utilized to make an online transaction. Any codes may be provided as one-time use codes (e.g., activated by manual input form a user) or time-based codes.

Buttons may be provided on a card that may be associated with, for example, different types of loyalty-based benefits. In this manner, a user may select the different type of reward the user desires to obtain for each purchase. In doing so, the user can select the type of reward that the user may found most useful for a particular period of time. For example, suppose a user is about to take an airplane trip and is only a few miles away from being awarded a free ticket. In such an instance, a user may find more utility in obtaining airline miles. Furthermore, allowing for multiple rewards on a card may, for example, provide a user with the ability to reduce the number of cards in his/her wallet while reducing card issuance costs at the card issuer.

Button 681 may be provided and may be associated with permanently printed information 671. Accordingly, for example, button 681 may be utilized by a user to instruct a processor that a particular reward associated with permanently printed information 671 is desired. Accordingly, the processor may communicate information through a reader communications component indicative of the user's desire to utilize a particular type of reward (e.g., RFID antenna, magnetic encoder, magnetic emulator, or IC chip). The processor may also display, for example, a code that may be entered online that is indicative of the type of reward a user desires. For example, a security code may be displayed on a display and a digit of this code may be associated to a particular reward. Alternatively, for example, a particular code may be representative of a particular reward. Alternatively still, for example, a particular code may take on a particular format such that an algorithm (e.g., a decryption algorithm) can both validate a code for security but also determine the type of reward that is desired.

For example, a security code may be generated based on one of a particular number (e.g., 4) of time-based encryption algorithms. Accordingly, a user may select a particular type of reward (or other feature) and an algorithm associated to that feature may be utilized to encrypt a private number. The code may be communicated through an online payment portion to a remote server. In turn, this remote server may decrypt the security code with all of the time-based encryption algorithms that could have been utilized. The algorithm that results in a particular private number may be determined to have been the algorithm selected by a user. In turn, the remote server may be able to determine the type of reward the user desires. In doing so, for example, information may be communicated through an online security code. Persons skilled in the art will appreciate that encryption algorithms may be chosen that, for example, do not result in the same encrypted number for any particular period of time.

Button 682 may be associated with permanently printed information 672. Button 682 may be associated with, for example, a type of reward. For example, button 682 may be associated with a cash-back reward. Accordingly, for example, a user may receive cash-back from a purchase if a cash-back reward is chosen. The cash-back may take many forms. For example, the user may receive a discount at the actual point-of-sale. Alternatively, the user's payment card account may be debited with the cash-back amount periodically (e.g., monthly or annually) or after a particular amount of cash-back has been accumulated (e.g., $100).

Button 683 may be associated with display 654. Display 654 may show a type of reward (e.g., charity). Similarly, button 683 may be associated with display 655. Display 655 may show a type of reward (e.g., reward points).

FIG. 6 also shows flow chart 690. Step 691 may be provided in flow chart 690, in which a transaction may be initiated. A transaction may be initiated in a variety of ways. For example, a card may be swiped through a payment card terminal. A user may select one of a variety of payment types. For example, a user may select to pay by a particular type of payment account (e.g., a credit account). Accordingly, step 692 may be initiated, in which a remote server determines from the received payment information that a user desired to pay with this particular payment account. Similarly, a user may select to pay via a different type of payment account (e.g., a debit account). Accordingly, step 693 may be initiated, in which a remote server determines from the received payment information that a user desired to pay with this different payment account. A user may also select to pay via a particular type of rewards. Accordingly, step 694 may be initiated, in which a remote server determines from the received payment information that a user desired to pay with this particular reward account. A user may pay for an item using one of multiple reward accounts. Step 695 may initiate to complete a transaction.

Figure 7:
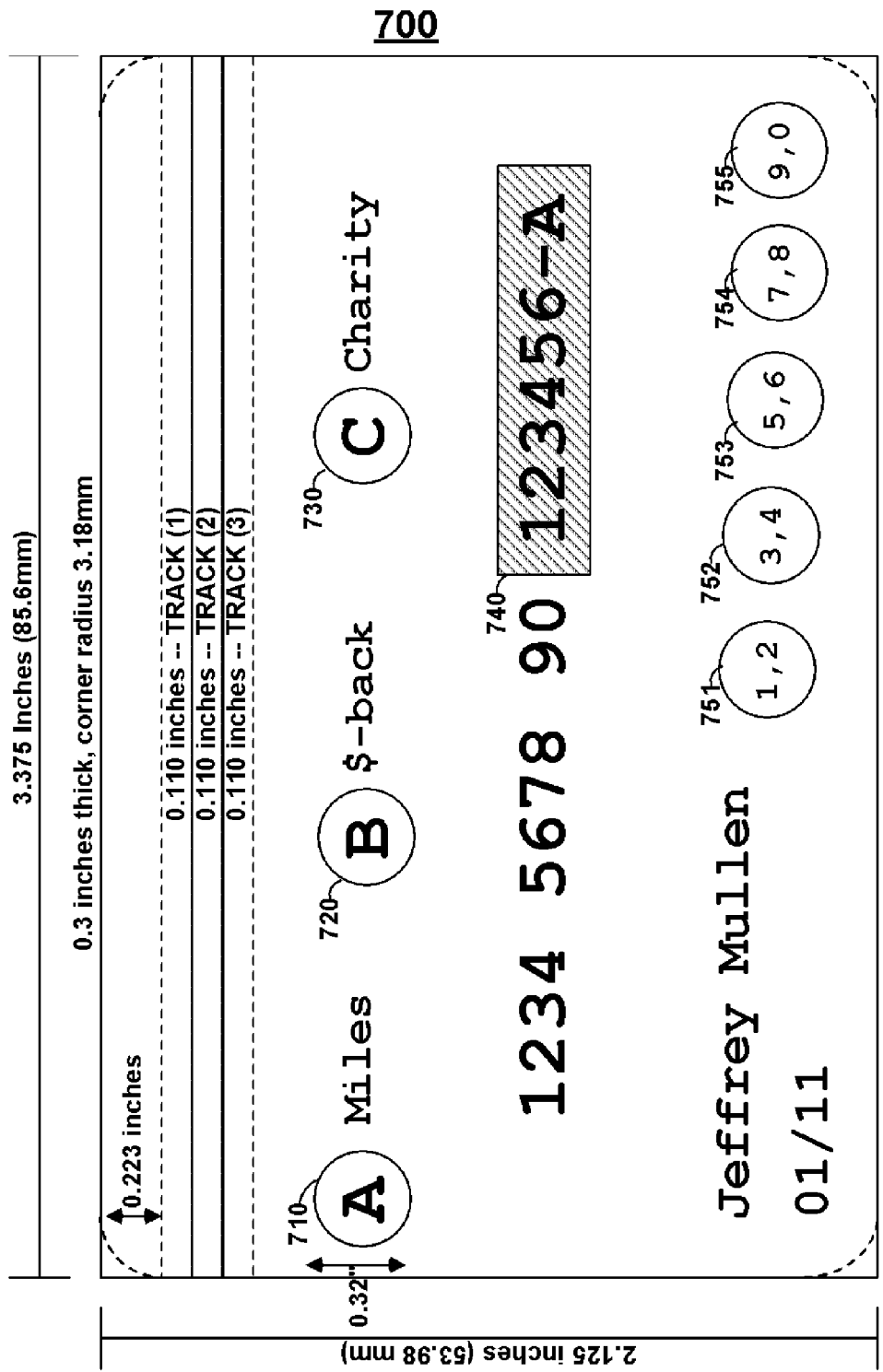
FIG. 7 is an illustration of a card constructed in accordance with the principles of the present invention.

FIG. 7 shows card 700 that may include buttons 710, 720, and 730. A user may utilize buttons 710, 720, and 730 to select a type of reward. For example, a user may select to purchase an item and have the purchase price utilized as part of a charity reward. In such a reward, for example, a particular percentage of the purchase price may be donated to charity. The user may be provided with an online or paper tax statement at the end of the year indicating how much money the user earned in rewards and provided to the charity.

Persons skilled in the art will appreciate that a user may be provided with a personalized webpage indicating to the user the types of rewards that were chosen for each transaction as well as summary information for the total amount of rewards earned during a period (e.g., a billing period) for each type of reward. A user may also be provided with the ability to transfer earned rewards to different types of rewards. Particular exchange rates may be provided for transferring rewards as well as transfer costs.

Display 740 may be provided on card 700. Display 740 may display, for example, a portion of an account number as well as information indicative of any user selection.

Buttons 751-755 may be provided, for example, such that a user may enter in various types of codes (e.g., unlocking codes, gift codes, discount codes, programming codes for changing the types of rewards on a card). Persons skilled in the art will appreciate that buttons 751-755 may also be utilized, for example, to select a reward. Accordingly, a user may enter in his personal unlocking code and then, when prompted, pick a particular button for a particular type of reward.

Figure 8:
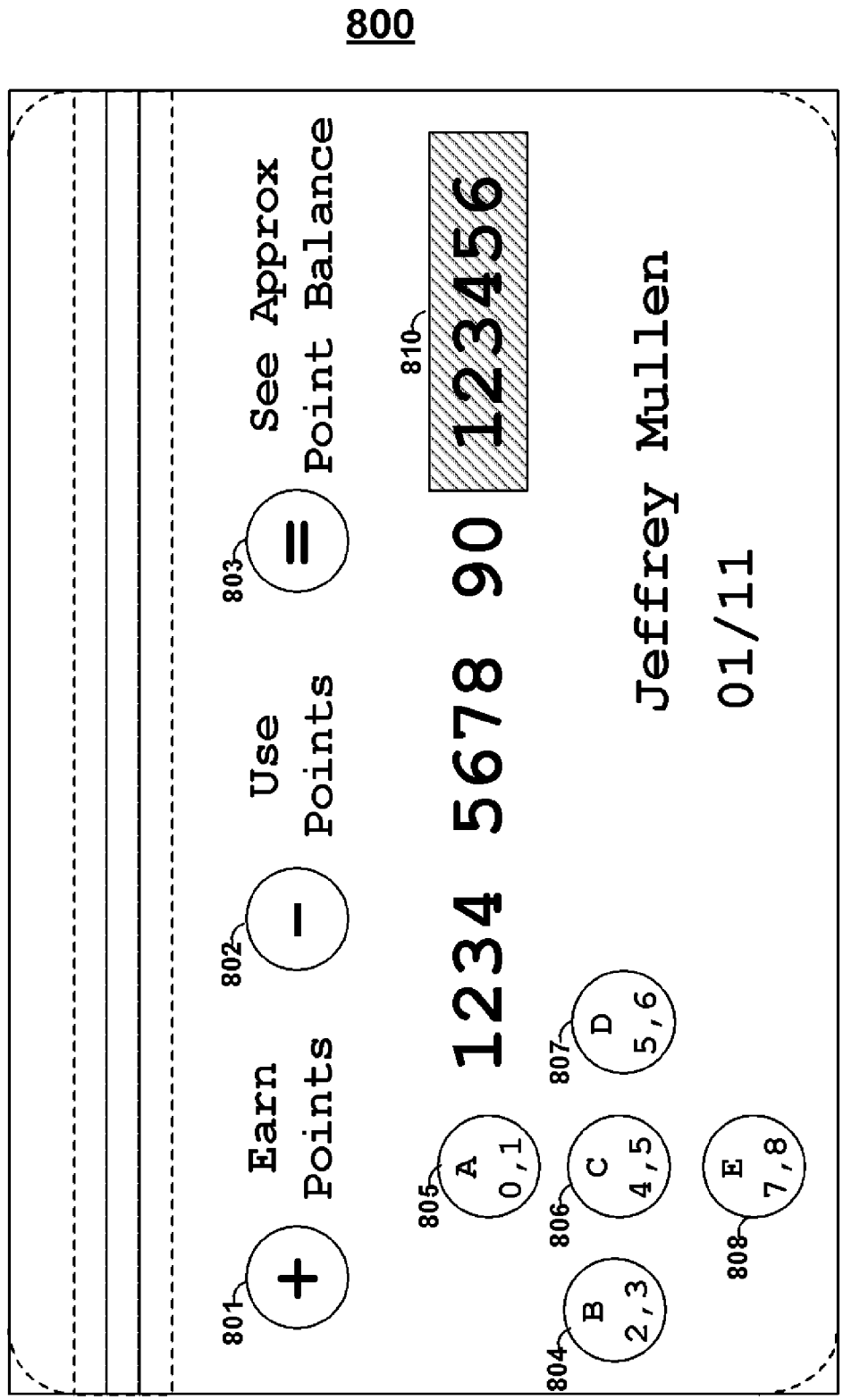
FIG. 8 is an illustration of a card constructed in accordance with the principles of the present invention.

FIG. 8 shows card 800 that may include buttons 804-808 for entering in various types of codes as well as making various types of user selections. Button 801 may be provided to allow a user, for example, to select that the user desires to earn points for a purchase. Button 802 may be provided for example, to allow a user to select that the user desires to spend points for a purchase. Persons skilled in the art will appreciate that a server may determine how many points are needed for a purchase, deduct that amount from a user's total, and, if applicable, deduct an amount of money from a particular payment account if the rewards points are exhausted with a remaining amount due.

Button 803 may be utilized by a user to see the user's point balance on display 810. Persons skilled in the art will appreciate that a card may receive balance information in a variety of ways. For example, a card may receive information via a magnetic emulator, IC chip, or an active RFID antenna.

Figure 9:
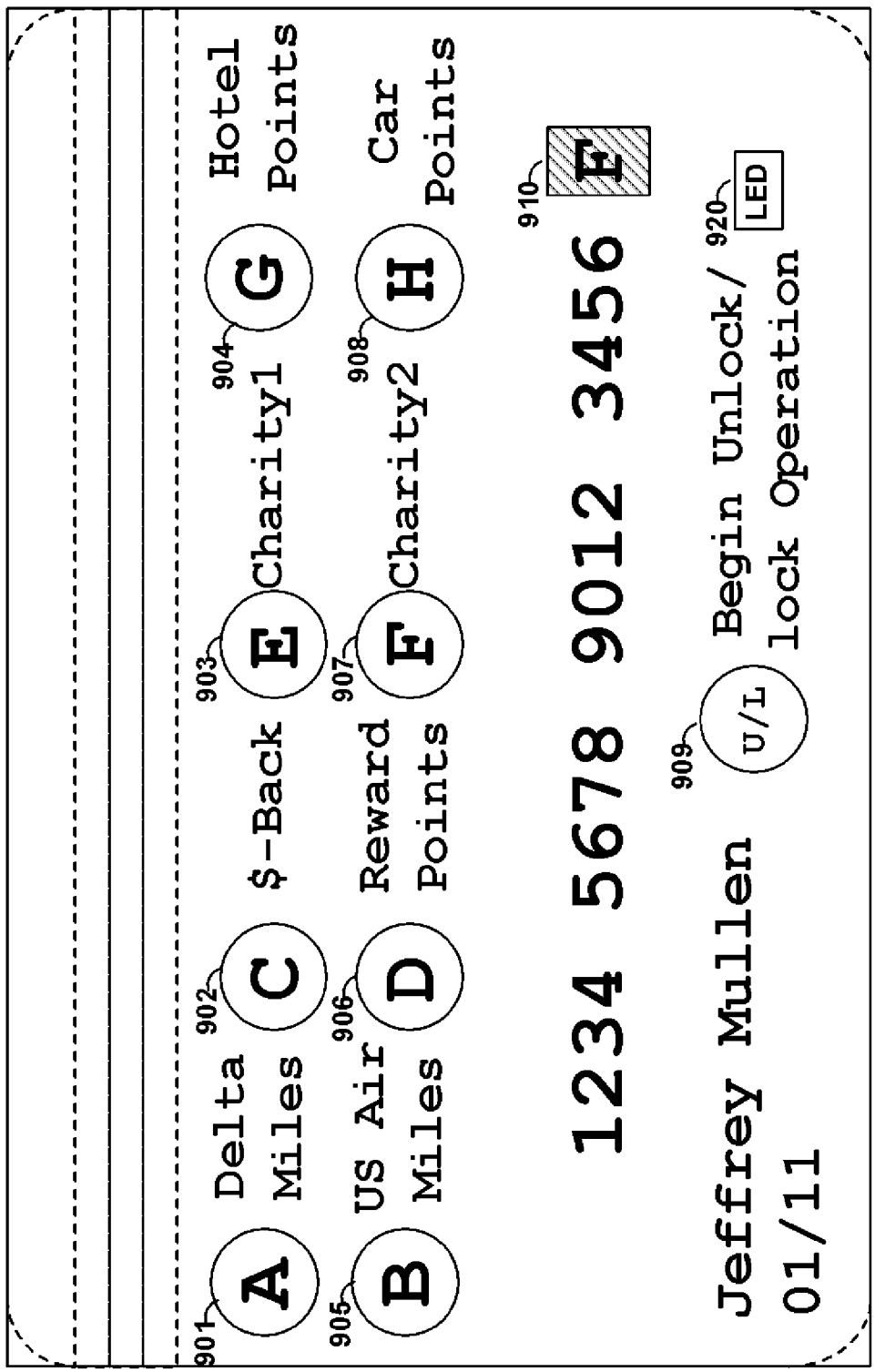
FIG. 9 is an illustration of a card constructed in accordance with the principles of the present invention.

FIG. 9 shows card 900 that may include buttons 901-908 for selecting various types of rewards. Display 910 may be utilized to indicate to a user the type of reward that was selected. For example, display 910 may be a one-character display. Button 909 may be utilized to indicate that a user desires to lock or unlock a card. A user may then utilize buttons 901-908 to enter in an unlocking code. Person skilled in the art will appreciate that a user may lock a card simply by pressing, for example, button 909. Light source 920 may be utilized, for example, to indicate to a user whether the card is locked or unlocked. For example, light source 920 may turn a particular color (e.g., GREEN) upon card 900 receiving an appropriate unlocking code. Light source may then, for example, periodically blink that color while a card is unlocked and the card's reader communicating components are activated for communication by a processor. Light source 920 may turn a different color (e.g., RED or ORANGE) if, for example, an incorrect code is entered. Light source 920 may similarly flash the same color as an incorrect unlocking code when the card locks (e.g., automatically or as a result of user input). Persons skilled in the art will appreciate that a card provided in the United States may be programmed to include GREEN as an unlocking color and RED as a locking color and a card provided in a different country (e.g., a European country) may provide RED as an unlocking color and GREEN as a locking color.

Figure 10:
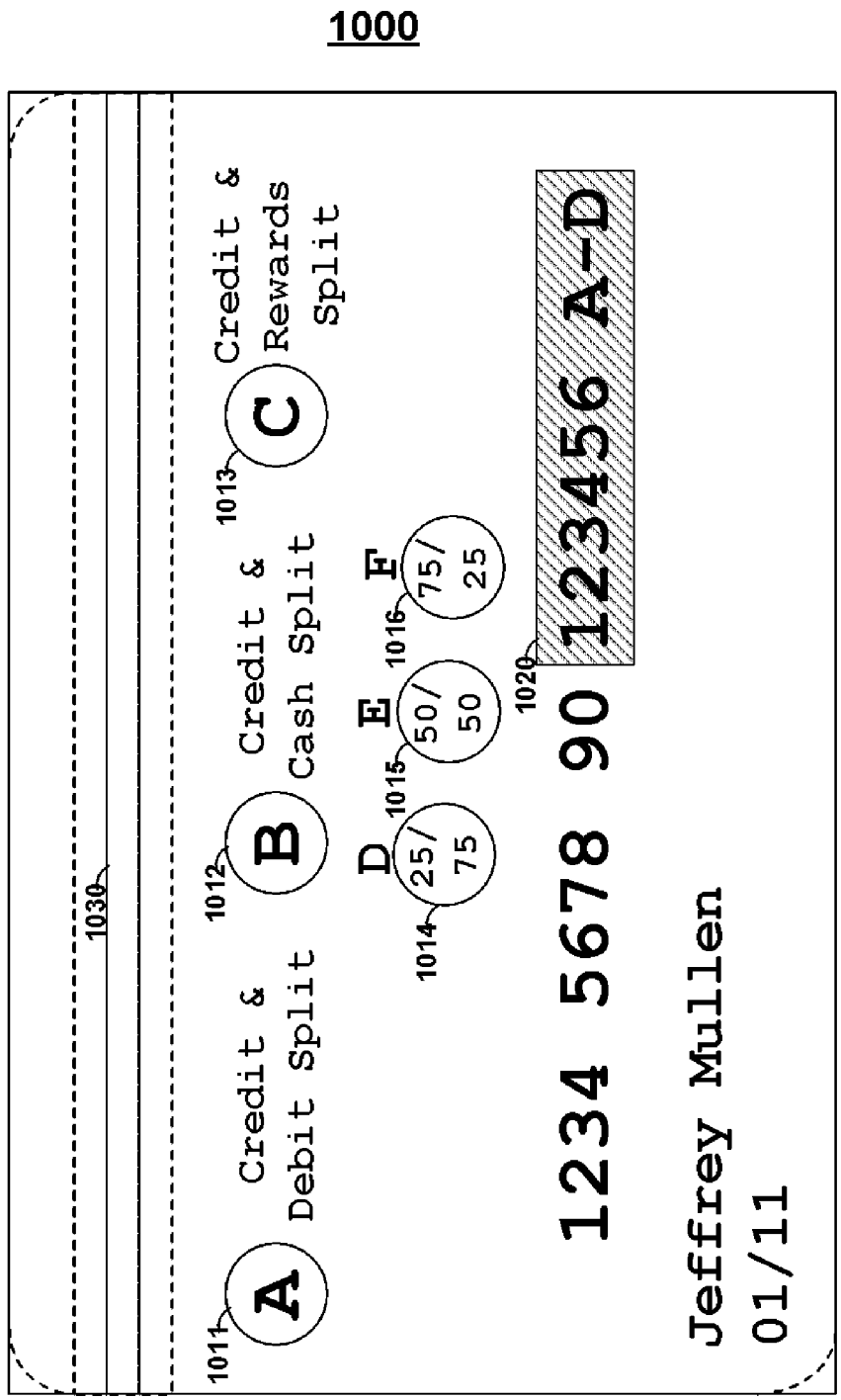
FIG. 10 is an illustration of a card constructed in accordance with the principles of the present invention.

FIG. 10 shows card 1000 that may include buttons 1011-1013. Button 1011 may be utilized to indicate to a processor that a user desires to split a bill between two different payment accounts. Button 1012 may be utilized to indicate to a processor that the user desires to split a bill between a credit and cash payment. Button 1013 may be utilized to indicate to a processor that the user desires to split a bill between credit and rewards points. Buttons 1014-1016 may be utilized, for example, to indicate the proportions of the split. Display 1020 may be utilized to display a portion of a payment account number as well as indicate the types of splits and the proportions of the splits that were selected by a user.

Figure 11:
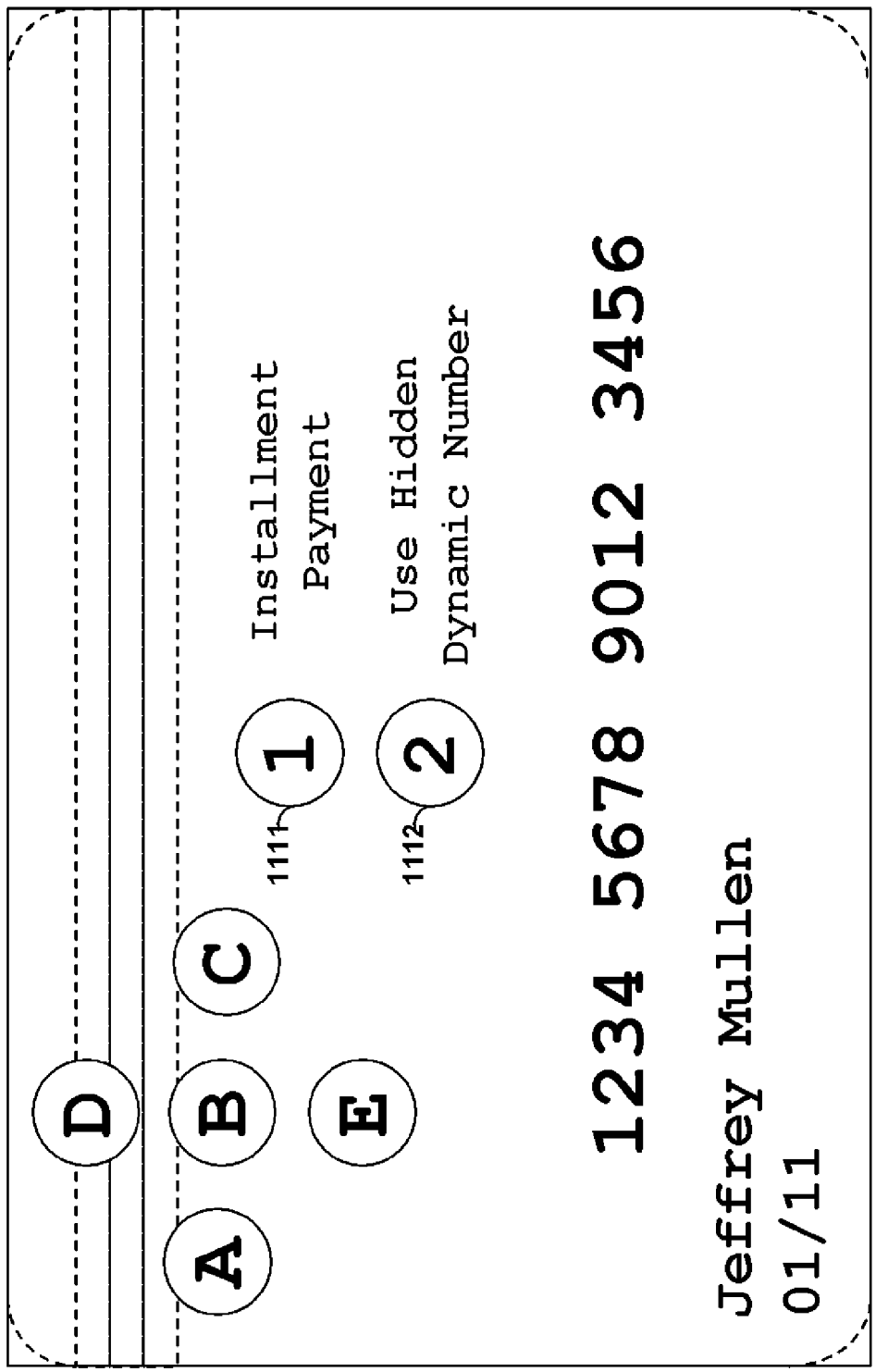
FIG. 11 is an illustration of a card constructed in accordance with the principles of the present invention.

FIG. 11 shows card 1100 that may include buttons 1111 and 1112. Persons skilled in the art will appreciate that a card may include any components (e.g., buttons, display, and light source) on either side of a card. Similarly, a magnetic emulator or encoder may be provided on either side of a card or, alternatively, in substantially the middle of a card. Any card may include a display or may not include a display.

Button 111 may be utilized to indicate a particular type of payment parameters—such as an installment payment. Additional buttons may be utilized to allow a user to select one of a variety of different installment payments. For example, numerical buttons may be included such that a user may enter in the amount of installments that are desired for a particular period of time. A button may be provided, for example, that allows a user to pay at his/her bonus time (e.g., a bonus paid by the user's employer). Button 1112 may be provided, for example, to indicate that a dynamic account number is desired to be used but that the number is desired to remain visually hidden. Accordingly, a dynamic account number may be provided via a magnetic emulator or stripe (e.g., or via an IC chip or RFID antenna).

Figure 12:
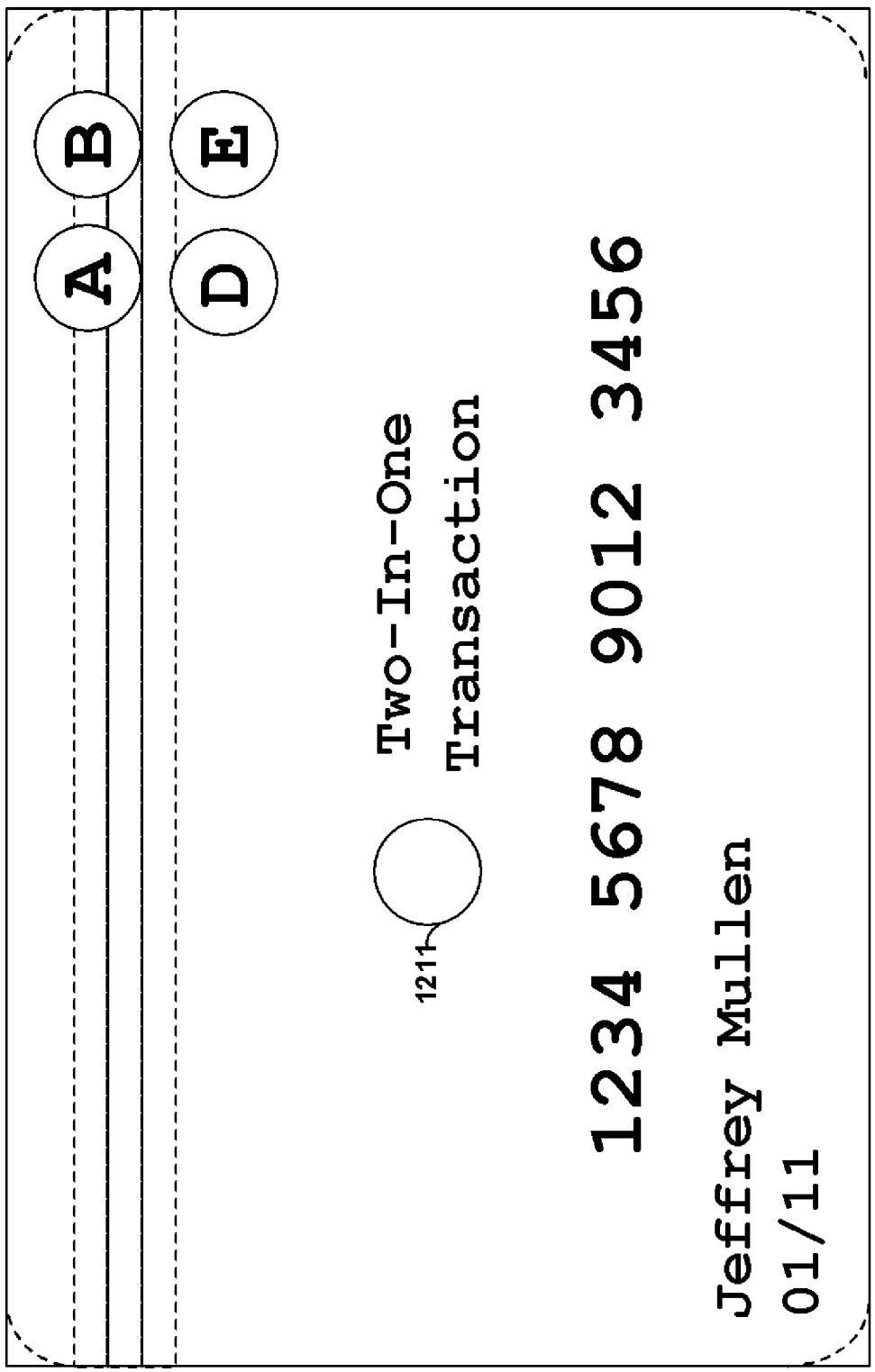
FIG. 12 is an illustration of a card constructed in accordance with the principles of the present invention.

FIG. 12 shows card 1200 and may include button 1211. Button 1211 may be utilized, for example, to provide two bundles of payment information serially to a reader via a magnetic emulator or magnetic encoder. Person skilled in the art will appreciate that a magnetic encoder communicating data serially may communicate data faster than a static magnetic stripe (e.g., over 2, 10, 20, or 30 times as fast) to a magnetic stripe reader. Accordingly, additional data may be communicated. Readers that are coupled, for example, to computers (e.g., cash-registers) with programming operable to receive serial bundles of payment information may receive multiple bundles of payment information with a single swipe. For example, if a user desires a split order between credit and debit, two bundles of payment information (one for credit and one for debit) may be communicated. Information may be included in the discretionary fields of both bundles of payment information indicative of the user's desire for a split order.

Figure 13:
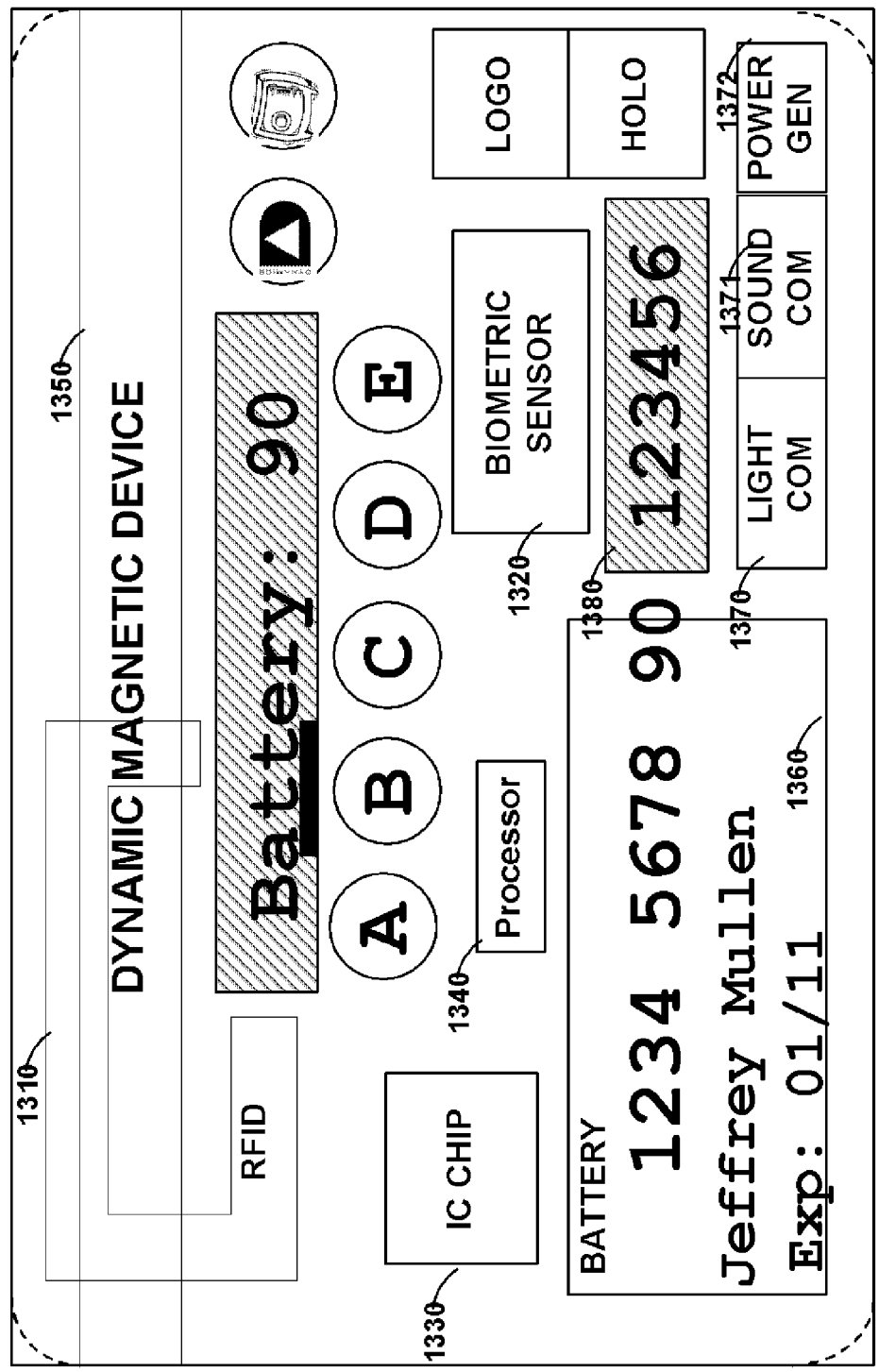
FIG. 13 is an illustration of a card constructed in accordance with the principles of the present invention.

FIG. 13 shows card 1300. Card 1300 may include any number of card reader communication devices such as a magnetic stripe encoder, magnetic emulator, RFID antenna, or IC chip. Card 1300 may also include a magnetic stripe. Card 1300 may include, for example, a serial magnetic emulator for track 1 data, a different serial magnetic emulator for track 2 data, and a static magnetic stripe for track 3 data.

Processor 1340 may control the data transmitted and received from any RFID antenna, IC chip, or magnetic emulator or encoder. Additionally, for example, an IC chip located on the card may be utilized to transmit and receive information to other communications components (e.g., an RFID). In this manner, a processor may, for example, drive information through a magnetic emulator while an IC chip may drive information through an RFID antenna. One or more memories may be provided to store payment information that is utilized by, for example, a card reader communications device.

Any number of batteries 1360 may be included on card 1300. Such batteries may be lithium polymer batteries and may, for example, be coupled together in a series configuration. Such batteries may be stacked or may lie adjacent to one another in card 1350. Batteries may be recharged from power received via a reader (e.g., via a power signal supplied to an IC chip or an electromagnetic field supplied to an RFID antenna).

One or more displays may be provided on card 1350. For example, display 1380 may be provided. Such a display may take many forms. For example, display 1380 may be an electrochromic display or an LCD display. Various forms of user interfaces, such as mechanical or capacitive buttons, may be provided on card 1350.

IC chip 1330 may be provided on card 1350 such that IC chip 1330 may transmit information to, and receive information by, an IC chip reader. Similarly, card 1350 may include RFID antenna 1310 which may, in turn, transmit information to, and receive information by, an RFID reader.

Card 1350 may include dynamic magnetic device 1350 that may communicate different information to a magnetic stripe reader. For example, dynamic magnetic device 1350 may be provided as a magnetic emulator or a magnetic stripe encoder. Additionally, for example, a magnetic stripe reader having a magnetic encoder may communicate information to, for example, a magnetic stripe emulator.

Biometric sensor 1320 may be provided. A biometric sensor may take many forms such as, for example, a fingerprint reader. A fingerprint reader may capture and compare partial fingerprints or full-fingerprints. Images may be initially stored during a setup procedure in which a user is prompted (e.g., via a display) to scan in his/her fingerprint. Such images may be retrieved (e.g., from a memory) and compared to fingerprints as new fingerprints are scanned to confirm a user's identity.

Light communication device 1370 may be included on card 1350 and may, for example, transmit and receive light-based information signals. Sound based communication device 1371 may be included on card 1350 and may, for example, transmit and receive sound-based information signals. Power generator 1372 may be utilized, for example, to harvest power such that a rechargeable battery located on card 1350 may be recharged. For example, such a power generator may harvest kinetic, thermal, solar, or electromagnetic energy and convert this energy to an electrical energy.

Figure 14:
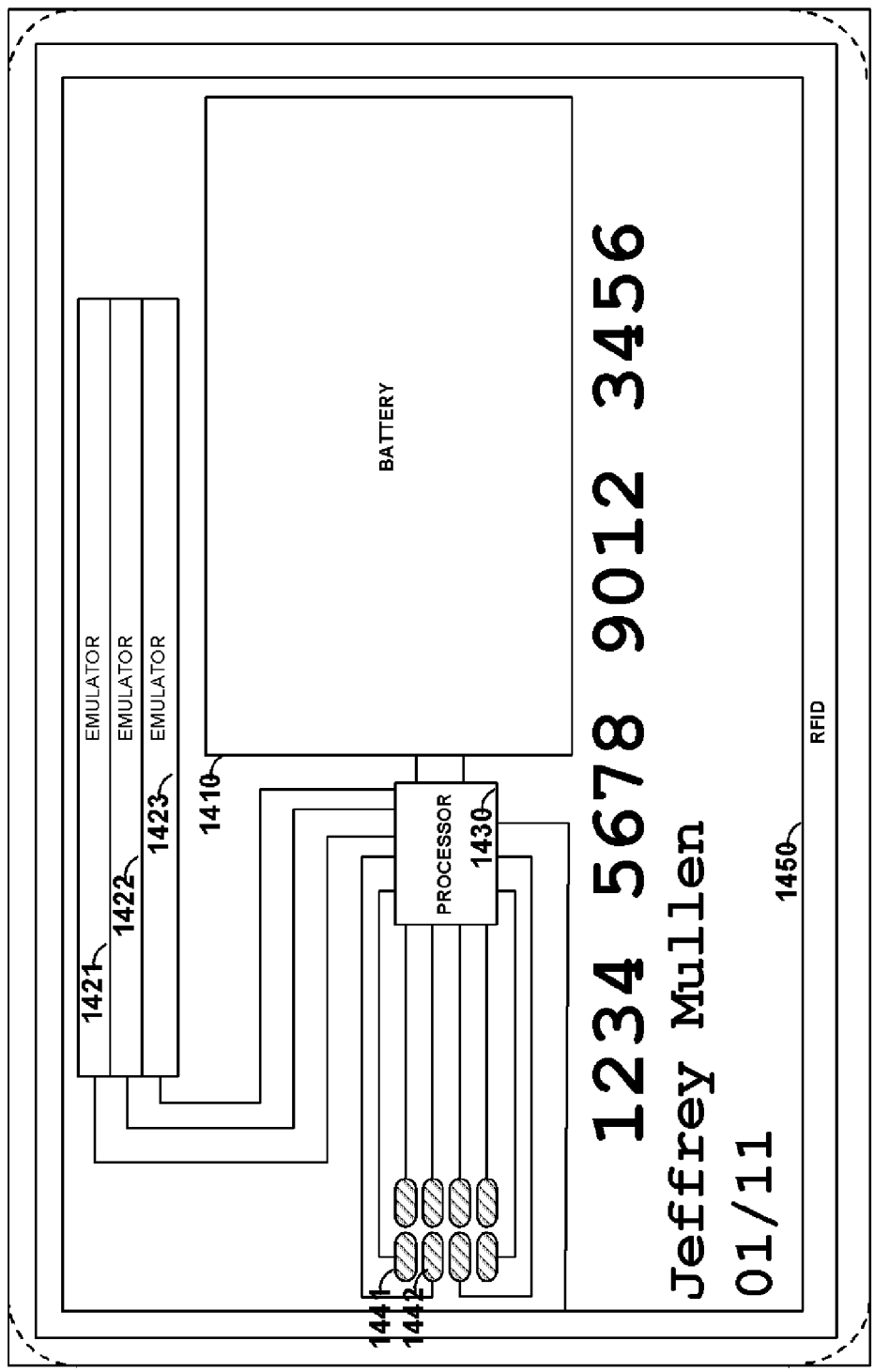
FIG. 14 is an illustration of a card constructed in accordance with the principles of the present invention.

FIG. 14 shows card 1400 that may include single track emulators 1421-1423 that communicate information serially to a magnetic read-head at the direction of processor 1430. Battery 1410 may be included to power processor 1430 and the rest of the circuitry of card 1400. Processor 1430 may also perform the functions of a payment IC chip. Particularly, for example, contacts (such as contacts 1441 and 1442) may be provided that may be able to couple with an IC chip reader. The contacts may route information between the IC chip reader and processor 1430. In doing so, for example, the cost of card 1400 may be reduced. Processor 1430 may be coupled to additional reader communications devices such as, for example, one or more different types of RFID antennas (e.g., RFID antenna 1450).

Figure 15:
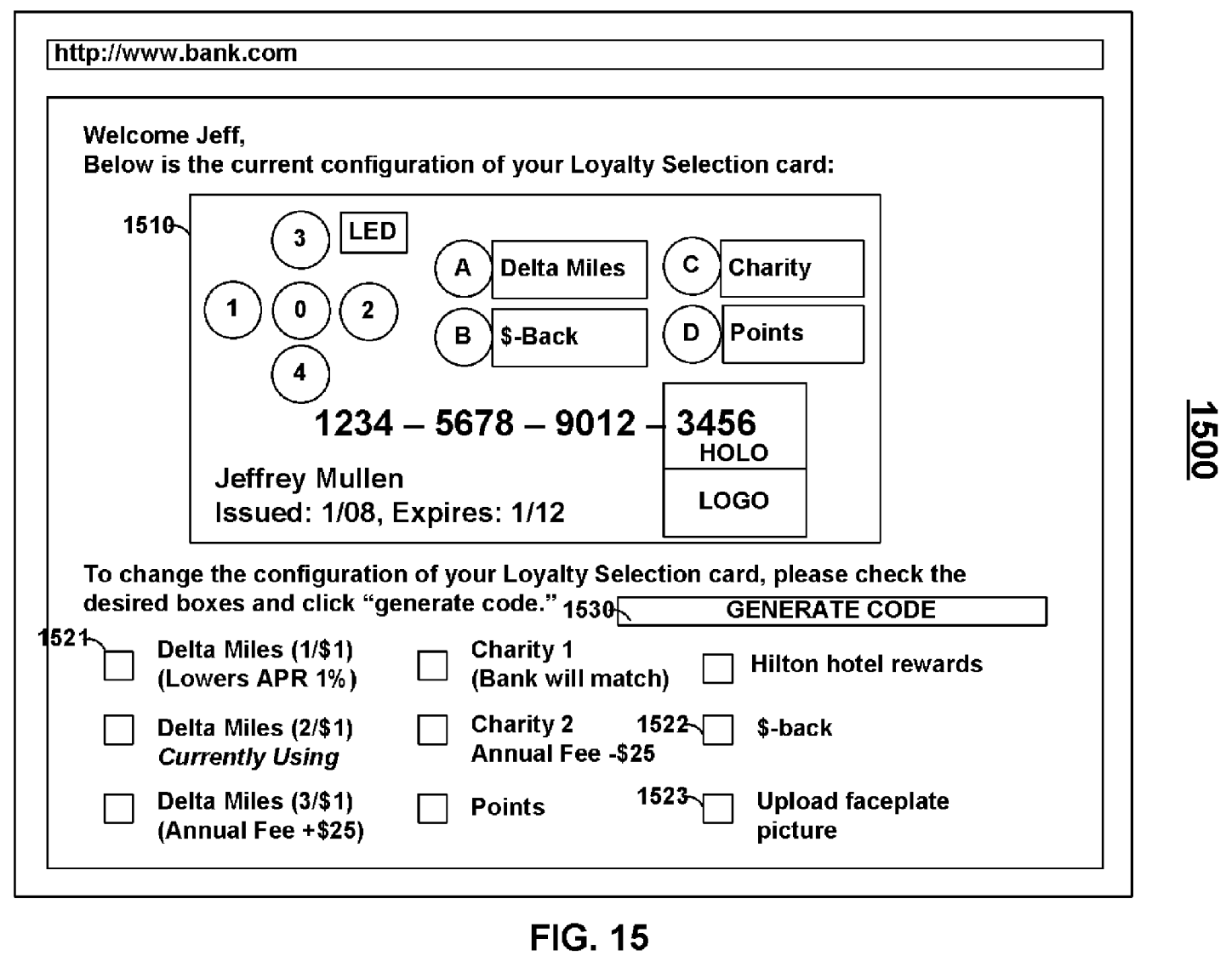

FIG. 15 shows website 1500. A card issuer may provide website 1500 to a user to allow that user to, for example, configure his/her payment card. For example, a user may select a number of features for a card using website 1500, be provided with a preview of a card that incorporates the selected features, and be provided with instructions on how to reconfigure the user's card. Website 1500 may also, for example, provide a user with a preview of the user's card as currently configured. For example, website 1500 may provide card layout 1510.

One type of feature that may be selected and configured by a user is that of a loyalty selection card. A user may select different types of rewards and generate a code, using virtual button 1530, for reconfiguring the user's card. Persons skilled in the art will appreciate that different rewards may change the general terms of a user's payment contract (e.g., credit contract). For example, a particular type of reward may raise or lower a user's APR, annual fee, late fees, or other costs. A user may also be charged a fee for reconfiguring a card (e.g., $1) or may be provided with a pre-determined number of reconfigurations before a cost is applied to a reconfiguration. A user may, for example, select reward 1521 and reward 1522. A user may upload a particular picture via upload 1523.

FIG. 16 includes webpage 1600. Persons skilled in the art will appreciate that the graphical user interface utilized by webpage 1600 may be utilized as a graphical user interface for a different medium (e.g., an application running on a mobile telephonic device). Similarly, card features may be provided on a mobile telephonic device either physically or embodied virtually. For example, a physical buttons may be provided as a virtual button on a graphical user interface displayed on a display screen of a mobile telephonic device.

Website 1600 may be initiated, for example, after a user has selected a configuration for his/her card. Such a configuration may associate, for example, different functionalities to different buttons as well as provide additional functionality. A user may be charged a monthly fee for particular features. For example, a user may be charged a periodic fee to introduce a dynamic account number capability to a card. As such, a user may configure a card to include both his/her personal and business accounts (e.g., via two buttons) and may configure a card to also include two types of rewards (e.g., miles and points). Accordingly, a user may select the type of card the user desires in a store as well as the type of rewards. If a dynamic account number capability was purchased (e.g., $5 or more per month or per year), then one or both of the accounts may be provided with time-based or use-based dynamic account numbers as well a time-based or use-based codes. Such codes may be displayed as well as communicated via a reader communications device (e.g., RFID, magnetic emulator or encoder, and IC chip). Displayed codes may be the same as codes communicated through a reader communications device or may be different codes.

Webpage 1600 may show an example of the reconfigured card via preview image 1610. Similarly, webpage 1600 may include either reconfiguration code 1630, virtual light transmission objet 1620, or both. Persons skilled in the art will appreciate that a card may have a table of possible configurations. Each entry of the table may correspond to a reconfiguration code. Accordingly, for example, a processor may reconfigure itself based on previously stored reconfiguration data. Alternatively, for example, the code for reconfiguration may be structured into a code that a user can enter manually or that can be wirelessly communicated to a card via signals (e.g., light-based signals from object 1620). Persons skilled in the art will appreciate that object 1620 may communicate information as light pulses and that a large amount of information may be communicated via object 1620. For example, a user may be directed to hold a card up to object 1620 for a particular period of time (e.g., approximately at least 10 seconds, 30 seconds, or at least 60 seconds or more). A user may be provided with a virtual button on the graphical user interface to initiate data transfer. A user may be provided with a virtual object (e.g., a red light may be replaced with a green light) on webpage 1600 after data is communicated. A card may provide a signal indicative that data was properly received (e.g., an LED may blink a particular color, such as GREEN, or a display may display indicia representative of successful receipt of data. Objects for communicating light pulses may be provided by any number of physical structures (e.g., an LED on a different payment card for card-to-card communications) or any number of virtual objects (e.g., on a television commercial).

Persons skilled in the art will appreciate that a reconfiguration may change the type of information that is communicated through reader communications devices as well as the functionality of any component (e.g., when an LED provides a particular color of light). For example, suppose a reconfiguration provides particular a particular buttons with a miles-based reward and provides a different button with a points-based reward. A magnetic encoder, magnetic emulator, IC chip (e.g., an EMV chip), or an RFID antenna may communicate a chosen reward by sending different data through the communications device.

The card may provide information indicative of the type of reward or functionality selected (e.g., a miles-based reward is desired). The card may provide information indicative of the button that was pressed. In this manner, a remote serve may have knowledge of the reconfiguration, receive the data indicative of the button that was pressed, utilize a look-up table to determine the functionality associated with the selected button for the particular reconfiguration, and utilize this retrieved information or forward this retrieved information to a different server.

Figure 17:
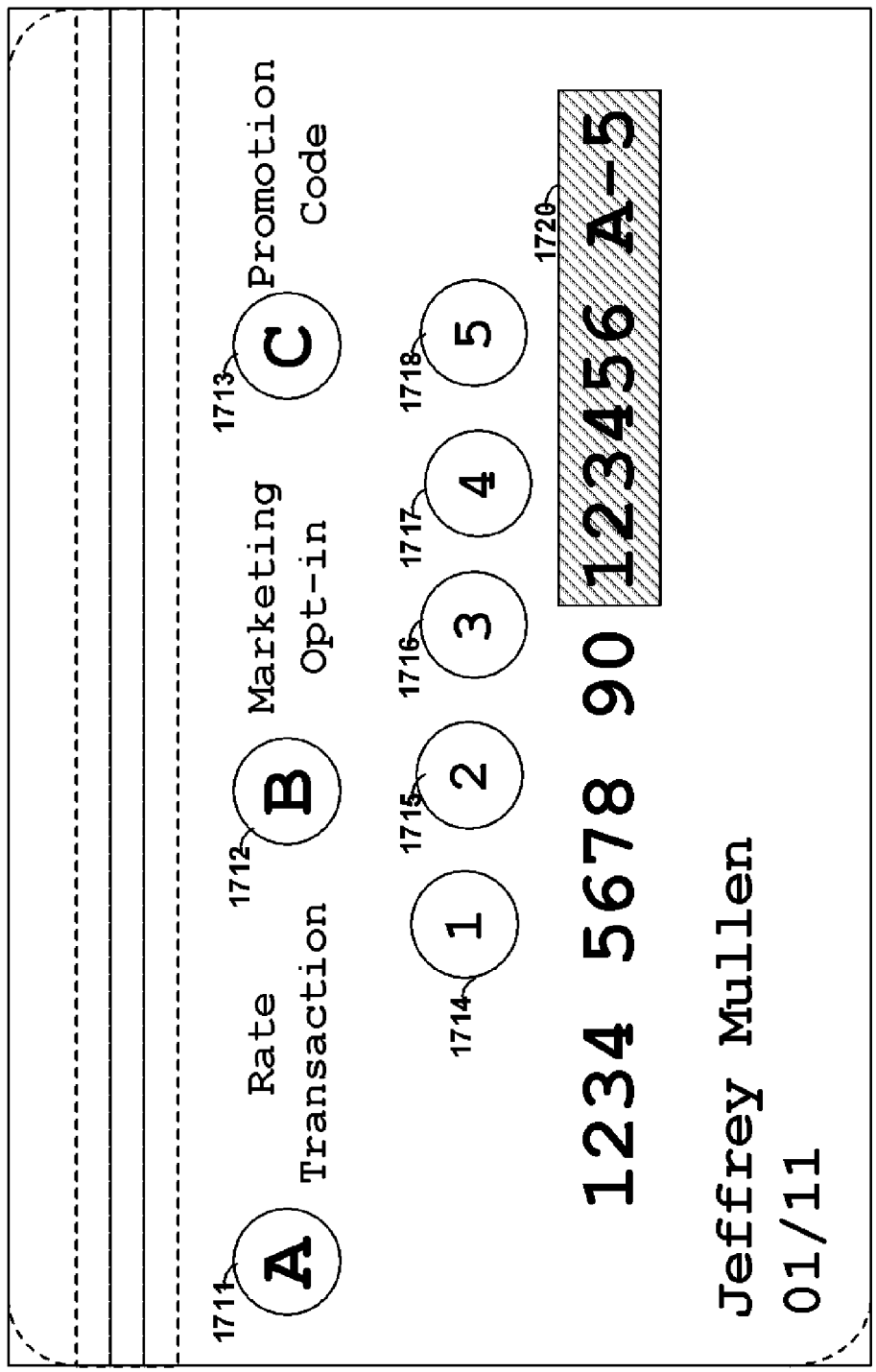
FIG. 17 is an illustration of a card constructed in accordance with the principles of the present invention.

FIG. 17 shows card 1700 that may include buttons 1714-1718 for entering data (e.g., a Personal Identification Number) and display 1720. Additional buttons may be included. For example, button 1711 may be included. A user may utilize button 1711 in order to rate a transaction. Accordingly, a user may press button 1711 and then provide a rating (e.g., a 1-5 rating) using buttons 1714. The rating may be indicative of the waitress, cashier, or purchase experience in general. Different buttons may be provided to rate different attributes of a store or purchase. A user may receive a promotional code on his/her receipt as a result of rating a transaction. Alternatively, for example, a user may be provided with a display (e.g., on a cash-register) for communicating the data wirelessly (e.g., via light-based signals). Alternatively, for example, a user may receive additional rewards for rating a purchase or store attribute (e.g., a waitress, cook, meal, wait lines, customer service). Such additional rewards may include additional points or miles such as a set amount of additional points or miles, points or miles associated with a cost of a purchase, or a multiplier of points or miles (e.g., double, tripe, or quadruple points or miles). A rating may also provide an immediate discount on a purchase (e.g., 20% or less than 20%). A user may view his/her ratings on a website associated with a user's account. A rating may be utilized by a card issuer to further prove that the appropriate user was in possession of a card at the time of a particular purchase. Display 1720 may indicate a selection of a functionality as well as any additional entered data (e.g., button "A" was pressed before button "5" was pressed).

Button 1712 may be included such that a user may select a marketing opt-in 1712. The selection of marketing op-in 1712 may result in personal information being provided to a merchant that, for example, completes an associated transaction. In exchange for the personal information, a merchant may provide the user with a number of benefits—such as rewards, discounts, or promotional codes. Personal information (e.g., telephone number, email address, mailing address, annual income, shopping history, age) may be pre-loaded onto card 1700 and communicated via a reader communications device separately from, or with, a payment account number and associated data for completing a payment purchase. For example, a cashier may be directed by the card to swipe the card twice—once to communicate personal information and a second time to communicate payment information. Alternatively, for example, information may be sent indicative of a user's desire to execute an opt-in marketing functionality. Accordingly, a remote server may recognize this received information, retrieve associated personal data, and forward this personal data to the appropriate location(s) (e.g., a remote server of the merchant). An opt-in marketing functionality may result in, for example, the emailing of a coupon to a user or the inclusion of a coupon on a webpage associated with the user's payment account.

Button 1713 may be included such that a user may select, for example, the entry or use of a promotional code. For example, a user may be provided with a promotional code on a receipt at time of checkout (e.g., as a result of using an opt-in marketing functionality). The promotional code may be entered into the card using buttons (or via wireless light-based signals) and may be communicated via a reader communications device (e.g., a dynamic magnetic stripe communications device comprising two magnetic emulators that simultaneously serially communicate different tracks of data to a magnetic stripe reader). The promotional code may be displayed on a display and the result of the promotional code may be displayed on a display. For example, the result of the promotional code (e.g., "Walmart −10%") may be displayed on a display next to a button. A user may press the associated button to provide the promotional code in the data communicated via a reader communications device. Software on the merchant-side may recognize the code and apply the code to a purchase. Such codes may automatically expire after a period of time, expire after a number of uses (e.g., via button presses, light-based signals acknowledging completion of a purchase, or detection of a data communication to a reader such as a detection of a read-head), or expire after a particular number of new codes are received, and a processor may delete the code from its memory. A display may be a bistable display or a non-bistable display.

Figure 18:
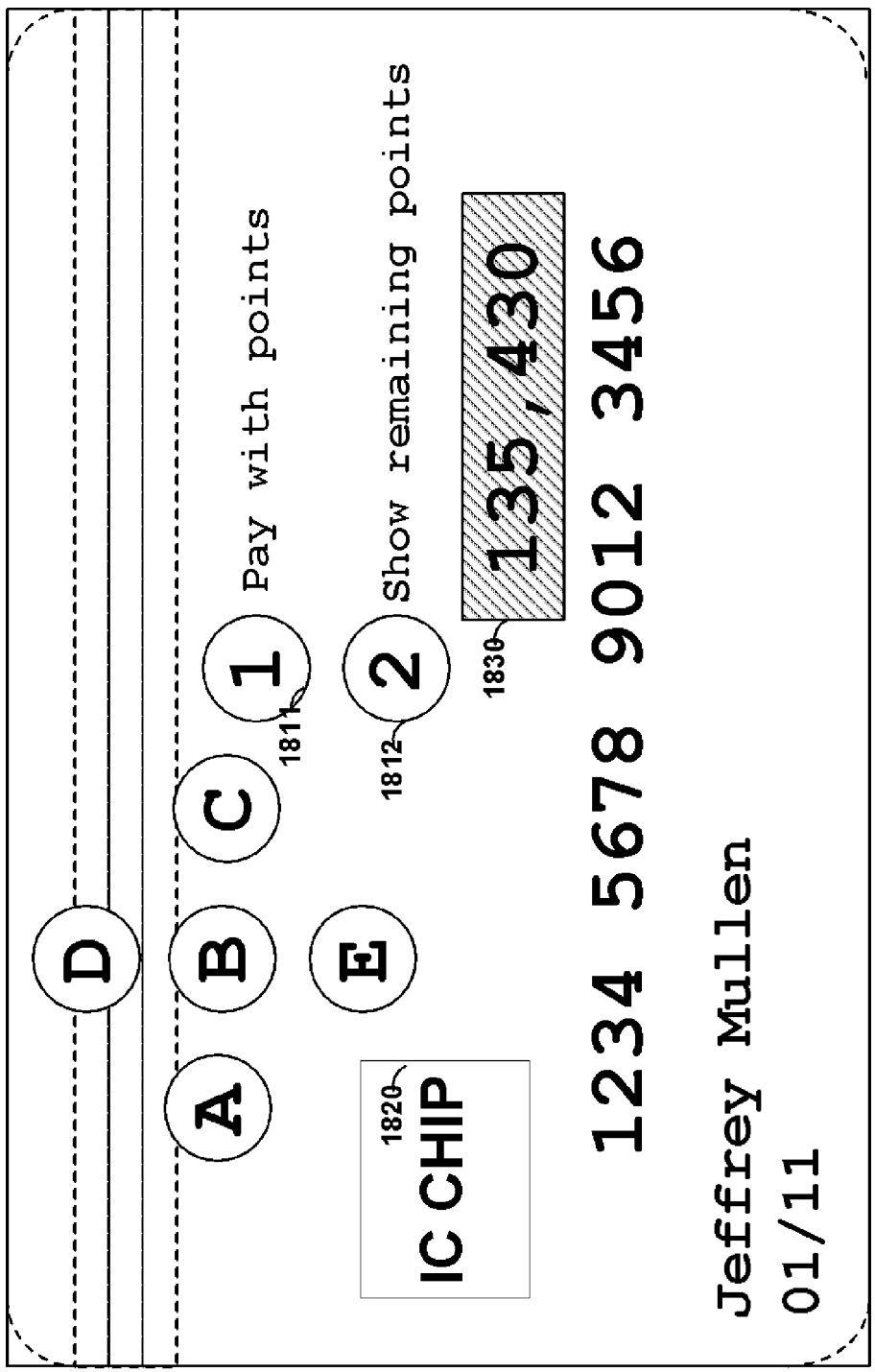
FIG. 18 is an illustration of a card constructed in accordance with the principles of the present invention.

FIG. 18 shows card 1800 that may include IC chip 1820 (e.g., an EMV chip), buttons 1811 and 1812, and display 1830. Button 1811 may be utilized to pay for a purchase with points. Button 1812 may be utilized to show the remaining number of points a user has on display 1830. A card may receive information from a variety of devices such as light sensors, IC chip 1820, an RFID antenna, or a dynamic magnetic device such as a magnetic emulator or a magnetic encoder. Persons skilled in the art will appreciate that IC chip 1820 may have conductive physical contacts on the surface of card 1800. IC chip 1820 may be, for example, approximately 3 mm×5 mm and may be located in the proximity of the center of the left side of the front of card 1800.

Figure 19:
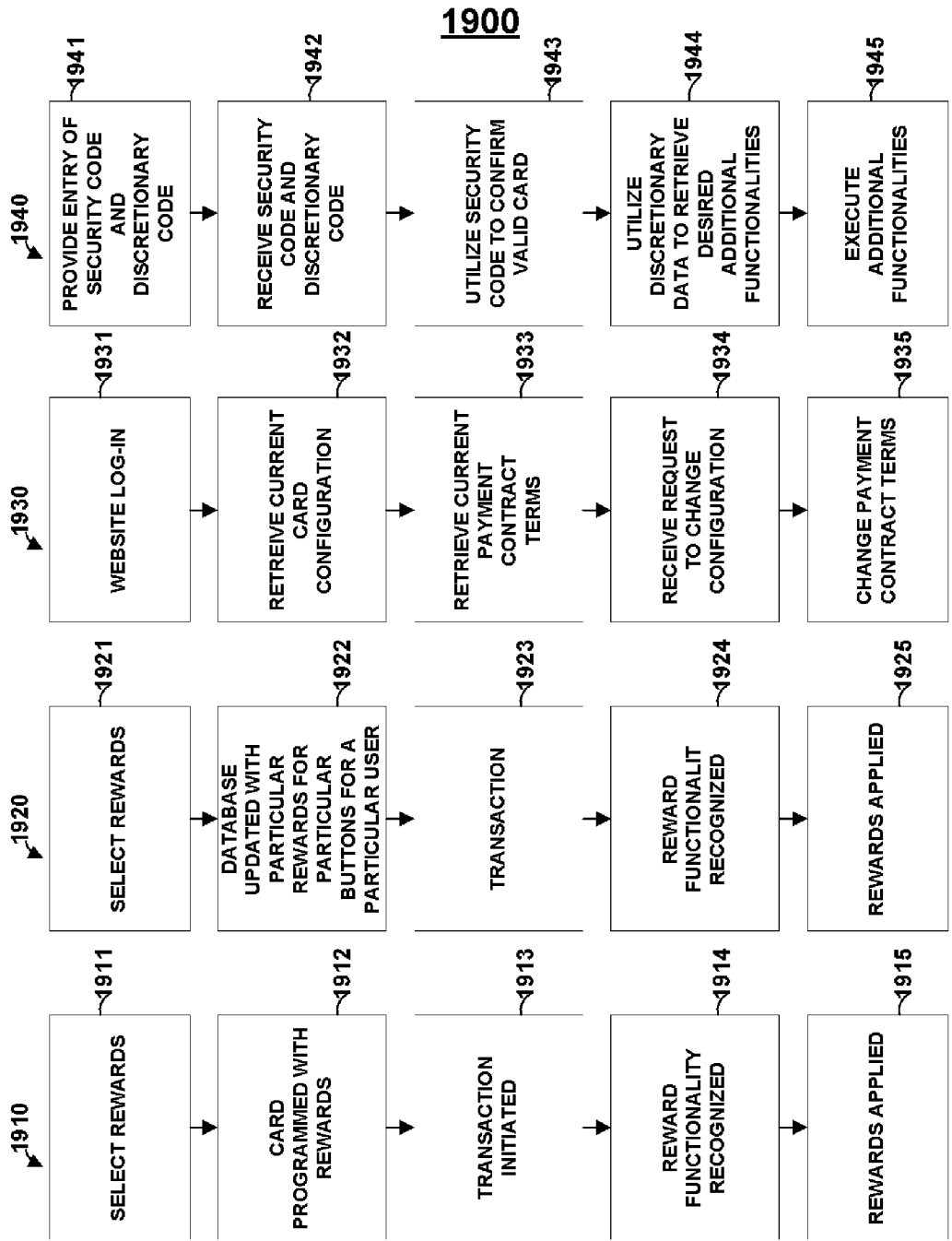
FIG. 19 is an illustration of payment flow charts constructed in accordance with the principles of the present invention.

FIG. 19 shows flow charts 1910, 1920, 1930, and 1940. Flow chart 1910 may be initiated with step 1910, in which one or more rewards (or other functionalities) are selected by a user. Such a selection may occur at the time the card is originally requested or when the card is in the passion of the user. Step 1920 may commence, in which the card is programmed with the various rewards (or other functionalities). Such programming may occur via a programming machine at a manufacturing or programming facility or by the user through the use of configuration codes or light-based signals.

Persons skilled in the art will appreciate that a card may be manufactured at a printed circuit board manufacturer. The board may then be send to an assembler. In, the assembler may put various components onto the board (e.g., solder on a display, chip, LEDs and buttons). Particular components may be fabricated at the printed circuit board manufacturer. For example, displays and buttons (e.g., capacitive buttons) may be fabricated as the board is fabricated. Additionally, reader communication devices (e.g., a magnetic emulator or RFID antenna) may be fabricated at the printed circuit board manufacturer. Microprocessors may be, for example, pre-programmed with the appropriate software before being sent to the assembler. Alternatively, software may be programmed into a card at the assembler. A card may be laminated before or after programming. A card may be partially programmed with certain data and later programmed with additional data. The different programming steps may occur at different locations. For example, an assembler may program code into a card so that the card can later receive personalization data from programming at a personalization facility. A personalization facility may also print indicia onto the surfaces of a card, provide holograms and static magnetic stripes onto a card. Lamination may also occur at a personalization facility. A card may be, for example, laminated and personalized except for programming of the card. Such a card may then be programmed at a different facility. Such programming may occur capacitively through the laminant to programming contacts of a microprocessor. The cards may then be mailed in envelopes with personalized letters to users. The card issuer may be notified that the cards were mailed. A user may utilize his/her card in a, POS, ATM, or call an activation telephone number to activate his/her card.

A transaction may be initiated in step 1913. Such an initiation may occur, for example, via interaction with a card reader or interaction with an online payment portal. Step 1914 may initiate when, for example, a remote server recognizes data indicative of a user's desire to earn a particular reward. For in-store purchases, such data may take the form of data communicated through a card reader. For online purchase or other manual entry purchases, the data may be provided in an account number, security code, or another code such as a discretionary data code. An online portal may request multiple codes for purchases. For example, an online portal may request entry of a security code or a discretionary data code. A card may thus display a security code and a discretionary data code. Such codes may, for example, change based on use or based on time. Rewards may be applied to the purchase in step 1925 (e.g., certain rewards may be earned for a particular purchase).

Flow chart 1920 may be provided in which step 1921 is initiated when, for example, a user selects a particular reward. Step 1922 may commence, in which a database may associated the selected rewards (or other functionalities) to particular buttons. A user may select which buttons are associated to which rewards. A user may also select a default application that does not require a button to initiate. For example, a user may select a default type of payment (e.g., a credit card number) as well as a default type of reward (e.g., miles for a particular airline). A database may store the configuration of a card. A transaction may be initiated in step 1923. Step 1924 may receive information of which button(s) were pressed and retrieve the current configuration of the card to determine the functionalities desired by the user. The remote server may apply those functionalities in step 1925.

Flow-chart 1930 may be included, in which a user logs into a website associated with the user's account in step 1931. Persons skilled in the art will appreciate that a payment account may include multiple statements for various types of payment a user includes on one or more payment cards. A payment account may include a combined statement for all types of payment (e.g., personal credit, business credit, and personal debit).

Step 1932 may commence in which the current configuration of a card is retrieved from a server in step 1932. Step 1933 may also retrieve the current payment terms for a user. Step 1934 may be initiated via the reception of a request to change the configuration of a card (or other device). Step 1935 may change the payment contract terms according to the configuration changes. A user may be provided with a confirmation screen to manually confirm the changes.

Flow chart 1940 may be included. Step 1941 may be initiated and a graphical user interface may be provided with text boxes for the entry of data. Such data may include, for example, payment card number, expiration date, address with zip code, name on card, a security code, and a discretionary data code. Step 1942 may commence when a remote server receives the data including the security code and discretionary data code. Such a graphical user interface may be provided on a website as part of an online payment process. Alternatively, for example, such a graphical user interface may be provided on a cash register application, portable telephonic device, or other device. Step 1943 may commence in which the card is validated as authentic using the security code. Step 1944 may commence, in which the discretionary data code is utilized to retrieve a variety of associated additional functionalities. These functionalities are executed in step 1945. Person skilled in the art will appreciate that discretionary data (e.g., such as discretionary data communicated through a reader communications device) may be embedded into a payment card number, address information, name information, as well as a security code. Accordingly, a remote server may remove the discretionary data from this information. Alternatively, for example, the use of the above data may be replaced to be that of a discretionary data use. For example, a user's name may be replaced by a code that does not include information associated with a user's name. A server may accordingly utilize this data to determine the discretionary or other data. For example, a security code may be utilized as discretionary data. Furthermore, such codes may include a parity bit or character. Moreover, for example, a limited number of operable codes may be utilized in order to reduce, for example, the mistaken entry and execution of a non-desired code. A confirmation screen may be provided to confirm correct entry of data. Such a confirmation screen may exist via a webpage or on a display of a card.

Figure 20:
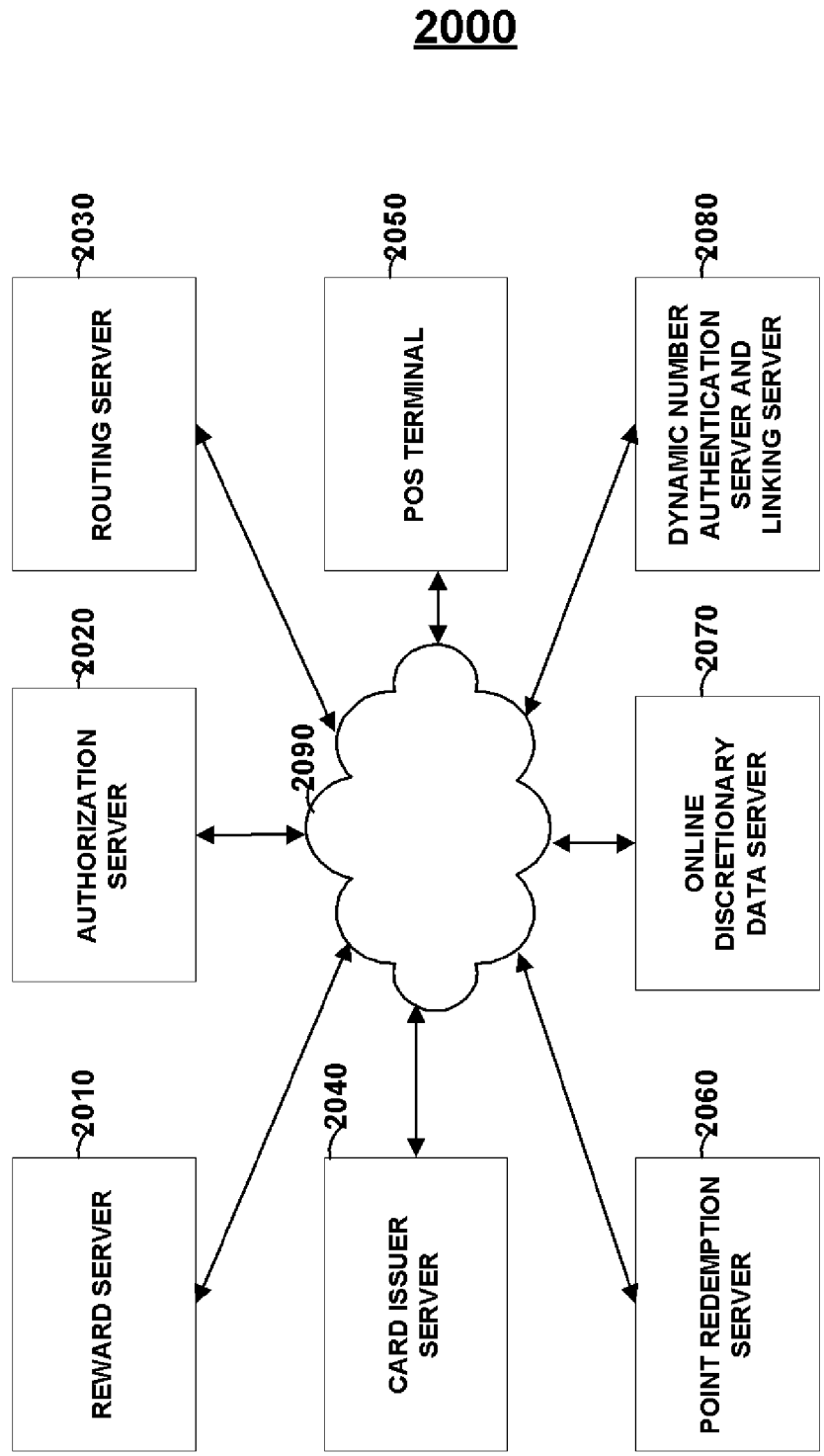
FIG. 20 is an illustration of a network topology constructed in accordance with the principles of the present invention.

FIG. 20 shows network topology 2000. Network topology 2000 may include communications network 2090. Communications network 2090 may include any number of communications servers, transmitters, and receivers. Communications network 2090 may also include, for example, any type of communication medium or multiple types of communication mediums. Communication mediums may include, for example, wireless or wire-based communications.

Reward server 2010 may be included in topology 2000. Reward server 2010 may perform a variety of functions. For example, reward server 2010 may receive information that was extract from a received information packet from a card reader. Reward server 2010 may determine the type of reward that was requested based on the extracted data. Reward server 2010 may execute a reward-based function such as point/reward management, point redemption/usage. For example, server 2010 may keep a running total of the amount of a particular reward (e.g., miles or points). Server 2010 may provide information regarding the total number of rewards, reward acquisition history, and reward usage history to other facilities. For example, this information may be communicated to a server at a facility managed by a card issuer such that the card issuer can incorporate this data into a webpage customized for a particular user.

Authorization server 2010 may be included in topology 2000. Authorization server 2010 may authorize an event—such as a payment or other transaction. Authorization server 2010 may receive card information (e.g., payment number and zip code) and may authorize this data. Routing server 2030 may be included. Routing server 2030 may route information based on the contents of the information. For example, routing server 2030 may receive payment information from point-of-sale device 2050 and look at the beginning digits of a payment number to determine which facility of a list of facilities to send the payment data. Such a routing server may transmit all of the information that was received or may extract information such that a smaller amount of information is forwarded to other facilities (e.g., extract the portions of the payment number used to route the payment information). The information may be forwarded to a variety of facilities such as, for example, a facility housing another routing server, an authorization sever, or a card issuer's server.

Card issuer server 2040 may be managed by the issuer of a particular payment card. Card issuer server 2040 may, for example, issue a webpage for a user or may perform particular functions such as online access verification (e.g., using an access code communicated via a display). Persons skilled in the art will appreciate that a card issuer may manage, for example, their own routing and authorization servers.

POS terminal 2050 may communicate information received from a card. POS terminal 2050 may take many forms such as, for example, a cash-register having a display and a magnetic stripe reader. POS terminal 2050 may receive information from topology 2000. For example, POS terminal may receive a signal indicative of the result of a transaction authorization (e.g., failed, verified, destroy card, or hold card and customer until a representative or authority arrives). Additional information may be communicated to the POS terminal such as, for example, a point or reward balance and information associated with a functionality of a card. Such information may be printed on a receipt directly or in a code form or communicated to the card (e.g., via light-based signals).

Point redemption server 2060 may be utilized to redeem rewards such as miles or points. Online discretionary data server 2070 may be included and may, for example, receive discretionary data and perform functions based on the received discretionary data. Such discretionary data may be received from multiple tracks of magnetic data where each track includes discretionary data. Such discretionary data may be received from an online purchase application that includes a window for receiving manually input discretionary data.

Dynamic number authentication and linking server 2080 may be utilized to authorize a dynamic payment card number (as well as dynamic codes). Such dynamic card numbers and codes may be based on use or on time. Server 2080 may also keep track of merchants that have utilized a number such that those merchants can utilize the number again at a future time (e.g., for period billing and one-click shopping).

Figure 21:
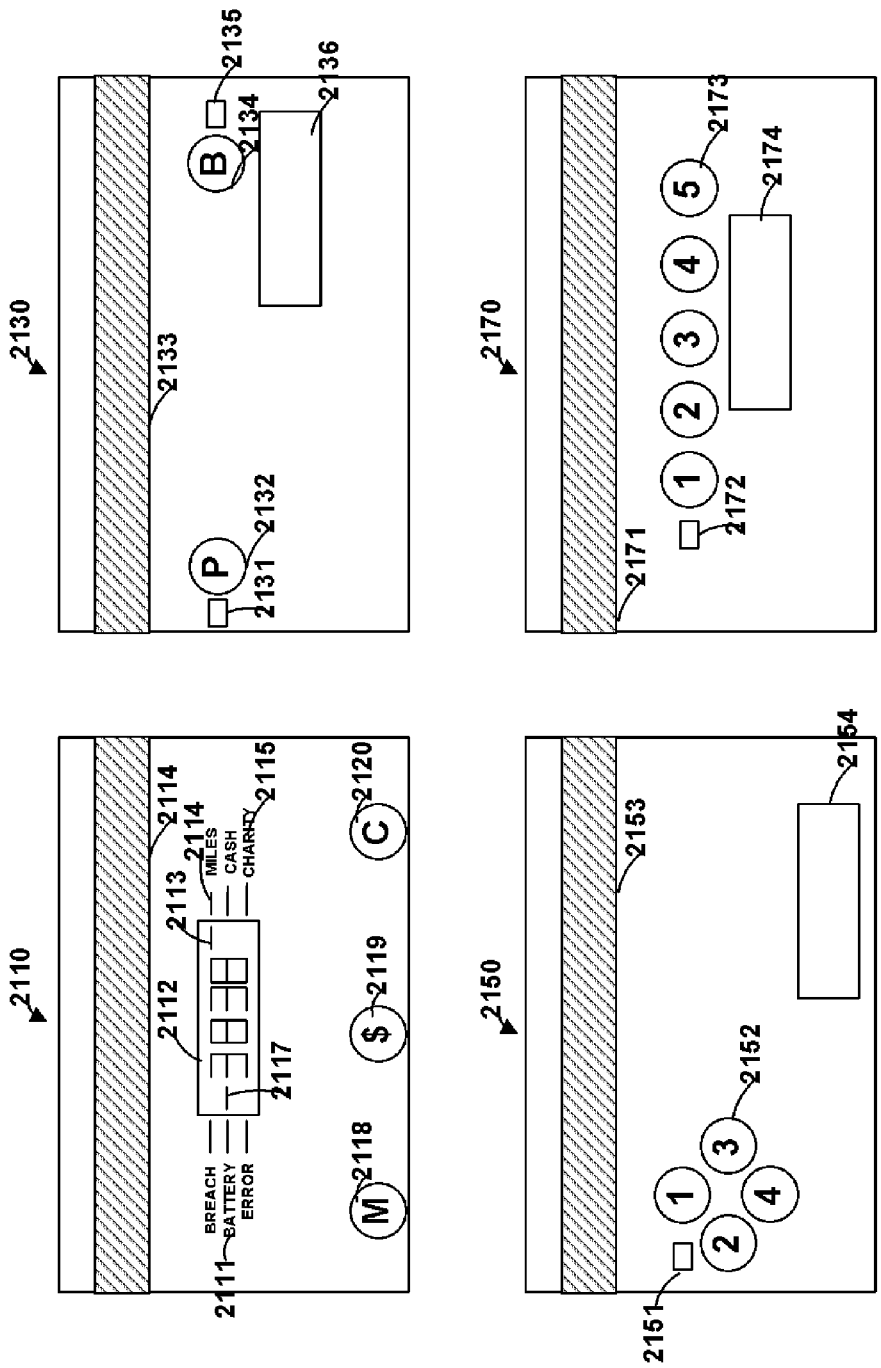
FIG. 21 is an illustration of cards constructed in accordance with the principles of the present invention.

FIG. 21 shows cards 2110, 2130, 2150, and 2170. Card 2110 may be included. Dynamic magnetic communications device 2114 may be provided on the front, back, or middle of a card. Dynamic magnetic communications device 2114 may be configured to provide electromagnetic signals, operable to be read by a magnetic stripe reader, to any one or both sides of card 2110. Display 2112 may be provided on the front or back of card 2110. Display 2122 may display discretionary data for use with online transactions. Data displayed on display 2110 may be entered into a security code input text box of an online purchase application or a discretionary data text box of an online purchase application. Card 2110 may include additional displays for a separate code (e.g., a security code) or for displaying other information such as a dynamic payment number.

Persons skilled in the art will appreciate that display 2112 may be a six-digit seven segment display. Accordingly, display 2112 may display 2112 may display four digits and may have fourteen segments to display. Such segments can be utilized to display information other than numbers. For example, segment 2113 may be utilized to indicate that a particular functionality is activated. Such a functionality may be associated with permanently written data 2114. For example, a user may activate button 2118 and segment 2113 may be displayed. Persons skilled in the art will appreciate that multiple segments on a digit display may be utilized at any given time. For example, a user may be provided with the ability to split the rewards earned by a purchase between two different types of rewards. For example, a user may press button 2118 to turn segment 2113 ON and press button 2118 again to turn segment 2114 OFF (and the associated functionality). Accordingly, a user may press button 2119 and an associated segment may be displayed or a user may press button 2120 and an associated segment may be displayed. A user may thus press buttons 2118 and 2120 and rewards earned may be split (e.g., 50/50 between miles and charity. A user may select all of the buttons and may evenly split rewards earned between those types. A user may be provided with the ability to select the distribution of rewards for every purchase (e.g., via additional buttons). Segments may also be utilized to display status information. For example, segment 2117 may be displayed to indicate that a battery is low or that a battery is not low. Permanent information 2111 may be printed in the proximity of segment 2117 to aide a user in understanding the functionality associated with segment 2117.

Card 2130 may be provided with, for example, display 2136, light source (e.g., LED) 2131, light source 2135, dynamic magnetic communications device 2133, button 2132 and button 2134. Display 2136 may display a partial payment number or a full payment number. Additional data may be displayed. For example, display 2136 may display a dynamic payment number and a static security code. Such a static security code may, for example, be constructed such that each number is printed as a single segment such that the number cannot be changed. Alternatively, the security code may be changed (e.g., based on time or based on use). A user may utilize button 2132 to display a particular payment number while utilizing button 2134 to display a different payment number. Such selected information may be communicated via magnetic communications device 2133 (along with other discretionary data). Discretionary data may also be displayed via a display for online use. Light source 2131 may be utilized to indicate that button 2132 has been activated. Light source 2134 may be utilized to indicate that button 2135 has been activated. Persons skilled in the art will appreciate that cards may show payment numbers (e.g., credit and debit card numbers) or other types of data. Such other types of data may include, for example, serial numbers for authorizing brokerage trades, video gaming numbers for accessing access to particular video games or video game characters, gambling numbers for different gambling accounts, or identification numbers for different loyalty programs (e.g., a grocery store chain's discount card and an electronic store's reward and discount card). Card 2130 may be pre-programmed with various numbers that are associated with particular buttons. Card 2130 may include buttons such that a user can reconfigure a card with different numbers either through manual input via buttons or wireless signals (e.g., light-based signals).

Card 2150 may be included that includes button 2152, light source 2151 and display 2154. A number may be hidden on display 2153 until an appropriate code is entered via buttons, which may be indicated via light source 2151.

Card 2170 may be included that includes button 2173, light source 2172 and display 2174. A number may be hidden on display 2153 until an appropriate code is entered via buttons, which may be indicated via light source 2151. Such a number may change based on time such that the number associated with the time period in which a correct PIN was entered is displayed on display 2174.

Persons skilled in the art will appreciate that any communications device may be added to a card. For example, an IC chip (e.g., EMV chip) may be added to card 2130 and may be utilized to provide information to an RFID antenna.

Persons skilled in the art will appreciate that data may be transferred, such as gift card and/or pre-paid card data, to a card in a variety of ways. For example, a card may be swiped a second time through a magnetic stripe reader that includes a magnetic stripe encoder. A coil on the card may be utilized to receive the information and provide the received information to a processor. In doing so, information may be loaded into the card. Similarly, an IC chip may be utilized to receive data as well as a passive or active RFID. Additionally, one or more microphones may be included to receive audio information that may be representative of data. Accordingly, for example, a user may hold his/her card, or other device, next to a device that is operable to transmit audio via a speaker (e.g., laptop, stationary computer, or mobile telephonic device). The audio information may be discerned by the card and utilized to load information into the card (e.g., a gift card or pre-paid card. An application may also be loaded that enhances the functionality of the card. Such an application may include, for example, a user's medical information such that medical information can be displayed via the card (or other device) during a medical emergency. Accordingly, applications and/or payment cards may be purchased online and a speaker may communicate information to a card. Similarly, the card may include a speaker for transmitting information such that bi-directional communications are established. A light detector may be provided on a card that may receive light pulses indicative of data. Accordingly, for example, a user may hold a card up to a display—such as the screen of a laptop, stationary computer, or mobile phone—and information may be communicated from the display to the card via the light detector. Similarly, a light source may be utilized to communicate information from one device to another. For example, a light source (e.g., LED) may be utilized to communicate information from one card to another. Similarly, a magnetic stripe reader may include a light source. A card may be positioned over the light source such that a light detector of the card is aligned with the light source to receive light. Accordingly, the light of a magnetic stripe reader (or other type of reader) may be utilized to communicate information back to a card. A user may utilize interfaces on the card (e.g., buttons) to initiate a transfer of data from one card to another card or from a device to a card. A variety of types of data may be communicated. For example, money may be communicated from one debit card to another debit card such that payments may occur between the cards. Accordingly, for example, the next time a card is utilized via a reader (e.g., a magnetic stripe reader) information of the transfer may be communicated to a server for processing. Light may be utilized to transfer data from a card to a computer using, for example, a camera (e.g., webcam) on the computer. Sound may be utilized to transfer data from a card to a computer using, for example, a microphone on the computer.

A display may also be utilized as an interface. For example, a display may include a contact and an electronic ink. The electronic ink may change colors in response to, for example, a particular electrical signal being supplied to the contact. A capacitive sensor may be coupled to such a contact, however, such that a user interaction with the contact may be sensed by the capacitive sensor. Accordingly, a card may include a display that can also receive user input. Persons skilled in the art will appreciate that a display may include multiple contacts. For example, a display may include multiple 7-segment (e.g., to display digits) or 11-segment, 14-segment, or 16-segment (e.g., to display alphanumerics) regions where each segment may be coupled to a capacitive sensor.

A biometric sensor may be placed on a card or other device. Such a biometric sensor may be, for example, a fingerprint reader. Accordingly, one or more fingerprints may be stored in the memory of a card and compared to scanned fingerprints. Different fingerprints may activate the card differently (e.g., utilize a different user's payment card info).

Persons skilled in the art will appreciate that a user's payment card number (e.g., credit card or debit card number)

does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed—but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time (or transaction or button press). Additionally, for example, a magnetic emulator (or multiple magnetic emulators) may magnetically communicate financial data that does not change with time. Such a card may reduce, for example, the effects of physical card theft and card cloning.

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

Figure 22:
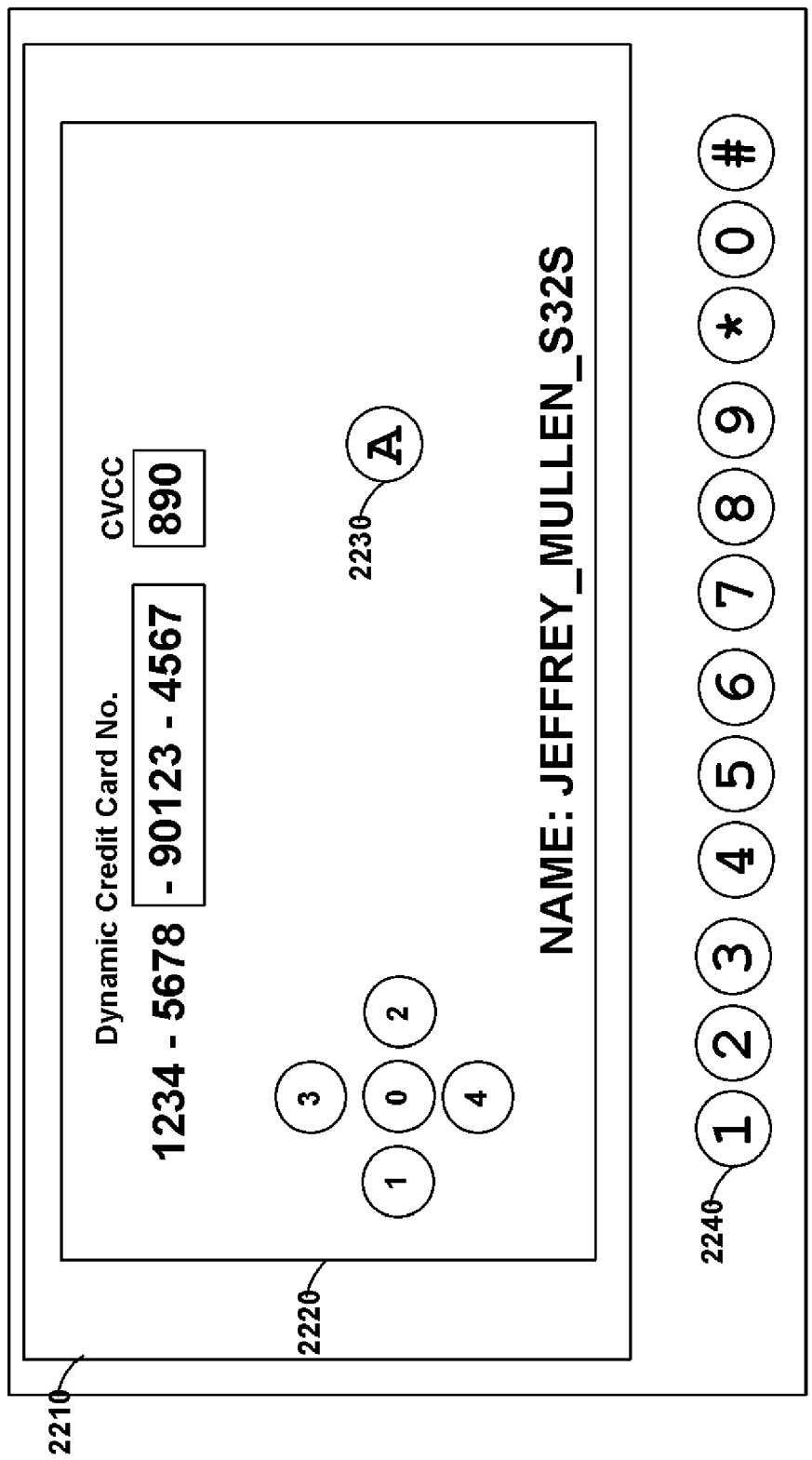
FIG. 22 is an illustration of a personal electronic device constructed in accordance with the principles of the present invention.

FIG. 22 shows personal electronic device 2200 which may be, for example, a portable telephonic device, portable media player, or any type of electronic device. Persons skilled in the art will appreciate that the functionality of a card may be provided on a personal device and displayed through a graphical user interface. Personal electronic device 2200 may include, for example, user inputs 2240 and display 2210. Virtual card 2220 may be displayed on display 2220. Display 2020 may be a touch-sensitive display such that, for example, virtual button 2230 may be provided on virtual card 2220. Persons skilled in the art will appreciate that cards may be provided as virtual cards and a user may interact with such virtual cards in order to provide a variety of functions. Personal electronic device 2200 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A payment device card comprising:
   a credit card account;
   a first button associated with earning a first reward for said credit card account for a merchant transaction; and
   a second button associated with earning a second reward for said credit card account for said merchant transaction, wherein selection of said first button causes information indicative of said first reward to be communicated through a communications device.

2. The payment device of claim 1, wherein said communications device comprises a dynamic magnetic stripe communications device.

3. The payment device of claim 1, wherein said communications device comprises an RF antenna.

4. The payment device of claim 1, wherein said communications device comprises an exposed chip.

5. The payment device of claim 1, further comprising:
   a processor;
   a battery; and
   a display.

6. The payment device of claim 1, wherein said first reward comprises miles.

7. The payment device of claim 1, further comprising a third button for earning a third reward for said credit card account for said merchant transaction.

8. A payment device comprising:
   a credit card account;
   a first button associated with receiving new rewards for said credit card account for a merchant transaction; and
   a second button associated with using acquired rewards for said credit card account for said merchant transaction, wherein selection of said second button causes information indicative of using a reward to be communicated through a communications device such that said acquired rewards are utilized to complete a purchase transaction.

9. The payment device of claim 8, wherein said communications device comprises a dynamic magnetic stripe communications device.

10. The payment device of claim 8, wherein said communications device comprises an RF antenna.

11. The payment device of claim 8, wherein said communications device comprises an exposed chip.

12. The payment device of claim 8, further comprising:
    a processor;
    a battery; and
    a display.

13. The payment device of claim 8, further comprising:
    an RF antenna; and
    a processor.

14. The payment device of claim 8, further comprising a third button.

15. A payment device comprising:
    a payment card account;
    a first button associated with earning a first reward for said payment card account for a merchant transaction;
    a second button associated with earning a second reward for said payment card account for said merchant transaction, wherein selection of said first button causes information indicative of said first reward to be communicated through a communications device; and
    a display for displaying indicia indicative of said selection of said first button.

16. The payment device of claim 15, wherein said indicia comprises an online payment code.

17. The payment device of claim 15, wherein said communications device comprises a dynamic magnetic stripe communications device.

18. The payment device of claim 15, wherein said communications device comprises an RF antenna.

19. The payment device of claim 15, wherein said communications device comprises an exposed chip.

20. The payment device of claim 15, further comprising:
    an RF antenna; and
    a processor.

21. The payment device of claim 15, further comprising a third button.

* * * * *